US012599739B2

(12) United States Patent
Yew et al.

(10) Patent No.: US 12,599,739 B2
(45) Date of Patent: Apr. 14, 2026

(54) PATIENT INTERFACE WITH FOAM CUSHION

(71) Applicant: RESMED ASIA PTE. LTD., Singapore (SG)

(72) Inventors: Robin Yew, Singapore (SG); Lik Tze Seet, Singapore (SG); Andrew James Bate, Sydney (AU); Kam Man Law, Sydney (AU)

(73) Assignee: RESMED ASIA PTE. LTD., Singapore (SG)

( * ) Notice: Subject to any disclaimer, the term of this patent is extended or adjusted under 35 U.S.C. 154(b) by 892 days.

(21) Appl. No.: 17/787,710

(22) PCT Filed: Dec. 20, 2019

(86) PCT No.: PCT/IB2019/061217
§ 371 (c)(1),
(2) Date: Jun. 21, 2022

(87) PCT Pub. No.: WO2021/123897
PCT Pub. Date: Jun. 24, 2021

(65) Prior Publication Data
US 2023/0039856 A1 Feb. 9, 2023

(51) Int. Cl.
*A61M 16/06* (2006.01)

(52) U.S. Cl.
CPC .... *A61M 16/0622* (2014.02); *A61M 16/0672* (2014.02); *A61M 16/0683* (2013.01); *A61M 2205/3344* (2013.01)

(58) Field of Classification Search
CPC .......... A61M 16/0622; A61M 16/0672; A61M 16/0683; A61M 2205/3344;
(Continued)

(56) References Cited

U.S. PATENT DOCUMENTS 4,782,832 A 11/1988 Trimble et al.
4,907,584 A 3/1990 Mcginnis et al.
(Continued)

FOREIGN PATENT DOCUMENTS

CN 1901962 A 1/2007
CN 101198379 A 6/2008
(Continued)

OTHER PUBLICATIONS

Office Action dated May 7, 2025 issued in Japanese Application No. 2024-101976 with English translation (6 pages).
(Continued)

*Primary Examiner* — Elliot S Ruddie
(74) *Attorney, Agent, or Firm* — NIXON & VANDERHYE, PC

(57) ABSTRACT

A patient interface is configured to deliver a flow of positive pressure respiratory gas to an entrance of a patients airways. The patient interface includes an elastomeric support wall forming at least part of a plenum chamber configured to receive the flow of positive pressure respiratory gas. The patient interface also includes an elastomeric support flange positioned at an end of the elastomeric support wall and extending radially inward from the support wall. The support flange has a flap portion at a central superior region of the support flange that extends further in the radially inward direction than the rest of the support flange. In addition, a foam cushion is mounted on the support flange. The foam cushion is configured to form a seal with the patients face and includes an attachment surface that is in contact with an outer surface of the support flange.

46 Claims, 32 Drawing Sheets

(58) Field of Classification Search

CPC .......... A61M 16/0069; A61M 16/1005; A61M 16/107; A61M 16/109; A61M 16/1095; A61M 16/16; A61M 16/161; A61M 16/208; A61M 2016/0027; A61M 2016/0039; A61M 2205/3368; A61M 2205/3375; A61M 2205/3553; A61M 2205/3561; A61M 2205/502; A61M 2210/0618; A61M 16/0816; A61M 2205/0216; A61M 16/06; A61M 16/0066; A61M 16/1055; A61M 16/1075; A61M 2016/003; A61M 2016/0661; A61M 2205/3365; A61M 2205/3334; A61M 2205/3584; A61M 2205/52; A61M 16/0666

See application file for complete search history.

(56) References Cited

U.S. PATENT DOCUMENTS

| | | | |
|---|---|---|---|
| 4,944,310 A | 7/1990 | Sullivan | |
| 5,687,715 A | 11/1997 | Landis | |
| 6,397,847 B1 | 6/2002 | Scarberry et al. | |
| 6,467,483 B1 * | 10/2002 | Kopacko | A61M 16/06 128/912 |
| 6,532,959 B1 | 3/2003 | Berthon-Jones | |
| 6,581,594 B1 | 6/2003 | Drew et al. | |
| 7,219,670 B2 | 5/2007 | Jones, Jr. et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 9,132,255 B2 | 9/2015 | Skipper et al. | |
| 9,320,865 B2 | 4/2016 | Ho | |
| 9,993,606 B2 | 6/2018 | Gibson et al. | |
| 10,166,357 B2 | 1/2019 | Veliss et al. | |
| 10,188,820 B2 | 1/2019 | Edwards | |
| 10,207,070 B2 | 2/2019 | Bayer et al. | |
| 10,500,362 B2 | 12/2019 | Henry et al. | |
| 11,020,558 B2 | 6/2021 | Kwok et al. | |
| 11,110,241 B2 | 9/2021 | Lockhart et al. | |
| 2001/0020474 A1 | 9/2001 | Hecker et al. | |
| 2003/0019496 A1 | 1/2003 | Kopacko et al. | |
| 2003/0196656 A1 | 10/2003 | Moore et al. | |
| 2006/0096598 A1 | 5/2006 | Ho et al. | |
| 2006/0130844 A1 | 6/2006 | Ho et al. | |
| 2007/0044804 A1 * | 3/2007 | Matula, Jr. | A61M 16/06 128/206.21 |
| 2007/0267017 A1 | 11/2007 | Mcauley et al. | |
| 2008/0110464 A1 | 5/2008 | Davidson et al. | |
| 2008/0302366 A1 | 12/2008 | Mcginnis et al. | |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2010/0006101 A1 | 1/2010 | Mcauley et al. | |
| 2010/0170516 A1 | 7/2010 | Grane | |
| 2012/0080035 A1 | 4/2012 | Guney et al. | |
| 2012/0138062 A1 | 6/2012 | Ho et al. | |
| 2012/0204879 A1 | 8/2012 | Cariola et al. | |
| 2012/0222680 A1 | 9/2012 | Eves et al. | |
| 2012/0285464 A1 | 11/2012 | Birch et al. | |
| 2013/0139822 A1 | 6/2013 | Gibson et al. | |
| 2013/0146060 A1 | 6/2013 | Ho et al. | |
| 2013/0199537 A1 | 8/2013 | Formica et al. | |
| 2013/0340763 A1 | 12/2013 | Eifler et al. | |
| 2014/0144448 A1 | 5/2014 | Eifler | |
| 2014/0174446 A1 | 6/2014 | Prentice et al. | |
| 2014/0196720 A1 | 7/2014 | Eury | |
| 2014/0216462 A1 * | 8/2014 | Law | A61M 16/0616 128/205.25 |
| 2014/0326246 A1 | 11/2014 | Chodkowski et al. | |
| 2015/0040911 A1 | 2/2015 | Davidson et al. | |
| 2015/0090266 A1 | 4/2015 | Melidis et al. | |
| 2015/0144140 A1 | 5/2015 | Eury et al. | |

| | | | |
|---|---|---|---|
| 2015/0151067 A1 | 6/2015 | Eury et al. | |
| 2015/0151071 A1 * | 6/2015 | Von Moger | A61M 16/0875 128/202.27 |
| 2015/0246198 A1 | 9/2015 | Bearne et al. | |
| 2015/0250971 A1 | 9/2015 | Bachelder et al. | |
| 2015/0335845 A1 | 11/2015 | Baiko et al. | |
| 2015/0374944 A1 | 12/2015 | Edwards | |
| 2016/0001029 A1 | 1/2016 | Bayer et al. | |
| 2016/0082213 A1 | 3/2016 | Eifler et al. | |
| 2018/0185598 A1 | 7/2018 | Olsen et al. | |
| 2018/0256843 A1 | 9/2018 | Eves et al. | |
| 2018/0256844 A1 | 9/2018 | Galgali et al. | |
| 2018/0272094 A1 | 9/2018 | Eves et al. | |
| 2018/0272095 A1 | 9/2018 | Eves et al. | |
| 2018/0280649 A1 | 10/2018 | Eves et al. | |
| 2019/0151590 A1 | 5/2019 | Guney et al. | |
| 2020/0121880 A1 | 4/2020 | Olsen et al. | |
| 2020/0384230 A1 | 12/2020 | Eves et al. | |
| 2022/0111171 A1 | 4/2022 | Eves et al. | |

FOREIGN PATENT DOCUMENTS

| | | | | |
|---|---|---|---|---|
| CN | 101242866 A | 8/2008 | | |
| CN | 101301505 A | 11/2008 | | |
| CN | 102753230 | 10/2012 | | |
| CN | 103945890 A | 7/2014 | | |
| CN | 104587580 A | 5/2015 | | |
| EP | 1258266 A1 | 11/2002 | | |
| EP | 1982740 A2 | 10/2008 | | |
| EP | 3095478 A1 | 11/2016 | | |
| GB | 2385533 A | 8/2003 | | |
| JP | 2008-518718 A | 6/2008 | | |
| JP | 2012-530561 | 12/2012 | | |
| JP | 2015-516241 A | 6/2015 | | |
| JP | 2016-504940 | 2/2016 | | |
| JP | 2017-527365 | 9/2017 | | |
| JP | 2018-526154 A | 9/2018 | | |
| JP | 2018-527154 A | 9/2018 | | |
| JP | 2019-508158 | 3/2019 | | |
| WO | WO 98/004310 A1 | 2/1998 | | |
| WO | WO 98/034665 A1 | 8/1998 | | |
| WO | WO 2000/078381 A1 | 12/2000 | | |
| WO | WO 2004/073778 A1 | 9/2004 | | |
| WO | WO 2005/063328 A1 | 7/2005 | | |
| WO | WO 2006/074513 A1 | 7/2006 | | |
| WO | WO 2006/130903 A1 | 12/2006 | | |
| WO | WO 2009/052560 A1 | 4/2009 | | |
| WO | 2010/009877 A1 | 1/2010 | | |
| WO | 2010/148453 A1 | 12/2010 | | |
| WO | WO 2010/135785 A1 | 12/2010 | | |
| WO | WO 2012/171072 A1 | 12/2012 | | |
| WO | WO 2013/020167 A1 | 2/2013 | | |
| WO | 2014/038959 A1 | 3/2014 | | |
| WO | 2014/062070 A1 | 4/2014 | | |
| WO | 2014/091360 A1 | 6/2014 | | |
| WO | 2014/110626 A1 | 7/2014 | | |
| WO | 2014/117227 | 8/2014 | | |
| WO | 2014/155329 A2 | 10/2014 | | |
| WO | 2015/009172 A1 | 1/2015 | | |
| WO | 2015/063283 A1 | 5/2015 | | |
| WO | 2016/032343 A1 | 3/2016 | | |
| WO | 2016/041019 A1 | 3/2016 | | |
| WO | 2016/054692 A2 | 4/2016 | | |
| WO | 2016/149769 | 9/2016 | | |
| WO | 2017/042717 A1 | 3/2017 | | |
| WO | 2017/049359 | 3/2017 | | |
| WO | 2017/049359 A1 | 3/2017 | | |
| WO | 2017/049360 | 3/2017 | | |
| WO | 2017/049361 | 3/2017 | | |
| WO | WO-2017120643 A1 * | 7/2017 | ........ | A61M 16/0683 |
| WO | 2017/185140 A1 | 11/2017 | | |
| WO | 2019/183680 A1 | 10/2019 | | |
| WO | 2019/183681 A1 | 10/2019 | | |

OTHER PUBLICATIONS

Extended European Search Report dated Jun. 17, 2025 issued in European Application No. 24215665.1 (12 pages).

(56)        References Cited

OTHER PUBLICATIONS

Office Action dated Jun. 16, 2025 issued in Chinese Application No. 201980103524.4 with English translation (16 pages).
Office Action dated Dec. 11, 2024 issued in Canadian Application No. 3,209,012 (5 pages).
Office Action dated Dec. 24, 2024 issued in Chinese Application No. 201980103524.4 with English translation (12 pages).
Office Action dated Nov. 14, 2022 issued in Japanese Application No. 2022-537761 with English translation (20 pages).
Extended European Search Report dated Jan. 27, 2023 issued in European Application No. 19957007.8 (7 pages).
Office Action dated Feb. 21, 2025 issued in Chinese Application No. 201980103524.4 with English translation (18 pages).
Examination Report dated Apr. 3, 2025 issued in Australian Application No. 2024204860 (2 pages).
Office Action dated Jan. 22, 2024 issued in Japanese Application No. 2023-060822 with English translation (9 pages).
"*Respiratory Physiology*", by John B. West, Lippincott Williams & Wilkins, 9th edition published 2012 (8 pages).
International Search Report dated Apr. 16, 2020 issued in International Application No. PCT/IB2019/061217 (6 pages).
Written Opinion of the International Searching Authority dated Apr. 16, 2020 issued in International Application No. PCT/IB2019/061217 (6 pages).
Written Opinion of the International Searching Authority dated Nov. 15, 2021 issued in International Application No. PCT/IB2019/061217 (6 pages).
International Preliminary Report on Patentability dated Mar. 29, 2022 issued in International Application No. PCT/IB2019/061217 (28 pages).
Office Action dated Apr. 28, 2021 issued in Chinese Application No. 201680066661.1 with English translation (16 pages).
Office Action dated Jun. 28, 2021 issued in Japanese Application No. 2018-533976 with English translation (6 pages).
Notice of Allowance dated Jun. 21, 2021 issued in Japanese Application No. 2018-533977 (3 pages).
Notice of Allowance dated Jul. 19, 2021 issued in Japanese Application No. 2018-533978 (3 pages).
Office Action dated Dec. 8, 2020 issued in Chinese Application No. 201680066661.1 with English translation (11 pages).
Office Action dated Oct. 5, 2020 issued in Japanese Application No. 2018-533976 with English translation (8 pages).
International Preliminary Report on Patentability for PCT/AU2016/050894, mailed Jan. 16, 2018, 11 pages.

Office Action dated Oct. 19, 2020 issued in Japanese Application No. 2018-533978 with English translation (8 pages).
Office Action dated Oct. 26, 2020 issued in European Application No. 16847658.8 (5 pages).
Notice of Reasons for Rejection dated Oct. 12, 2020 issued in Application No. 2018-533977 with English translation (15 pages).
Office Action dated Oct. 15, 2020 issued in European Application No. 16847657.0 (5 pages).
Office Action dated Feb. 3, 2020 issued in Chinese Application No. 201680056156.9 with English translation (15 pages).
Office Action dated Feb. 3, 2020 issued in Chinese Application No. 201680061003.3 with English translation (21 pages).
Office Action dated Jan. 28, 2020 issued in U.S. Appl. No. 15/759,985 (17 pages).
Office Action dated Feb. 25, 2020 issued in U.S. Appl. No. 15/761,168 (22 pages).
Extended European Search Report dated May 10, 2019 issued in European Application No. 16847657.0 (8 pages).
International Search Report for PCT/AU2016/050896, mailed Jan. 3, 2017, 8 pages.
Written Opinion for PCT/AU2016/050896, mailed Jan. 3, 2017, 7 pages.
Written Opinion of the ISA for PCT/AU2016/050894, mailed Dec. 12, 2016, 4 pages.
Written Opinion of the IPEA for PCT/AU2016/050894, mailed Oct. 27, 2017, 6 pages.
International Preliminary Report on Patentability for PCT/AU2016/050896, mailed Jan. 9, 2018, 189 pages.
International Search Report for PCT/AU2016/050895, mailed Jan. 12, 2017, 15 pages.
Written Opinion of the ISA PCT/AU2016/050895, mailed Jan. 12, 2017, 12 pages.
Written Opinion of the IPEA for PCT/AU2016/050895, mailed Oct. 23, 2017, 10 pages.
International Preliminary Report on Patentability for PCT/AU2016/050895, mailed Jan. 22, 2018, 221 pages.
Extended European Search Report dated May 13, 2019 issued in European Application No. 16847658.8 (11 pages).
Partial Supplementary European Search Report dated May 13, 2019 issued in European Application No. 16847659.6 (15 pages).
International Search Report for PCT/AU2016/050894, mailed Dec. 12, 2016, 7 pages.
Chinese Office Action dated Jan. 14, 2026, received in CN Application No. 201980103524.4, 108 pp.

* cited by examiner

Nasal cavity

Oral cavity

Larynx

Vocal folds

Oesophagus

Trachea

Bronchus

Lung

Heart

Diaphragm

Alveolar sacs

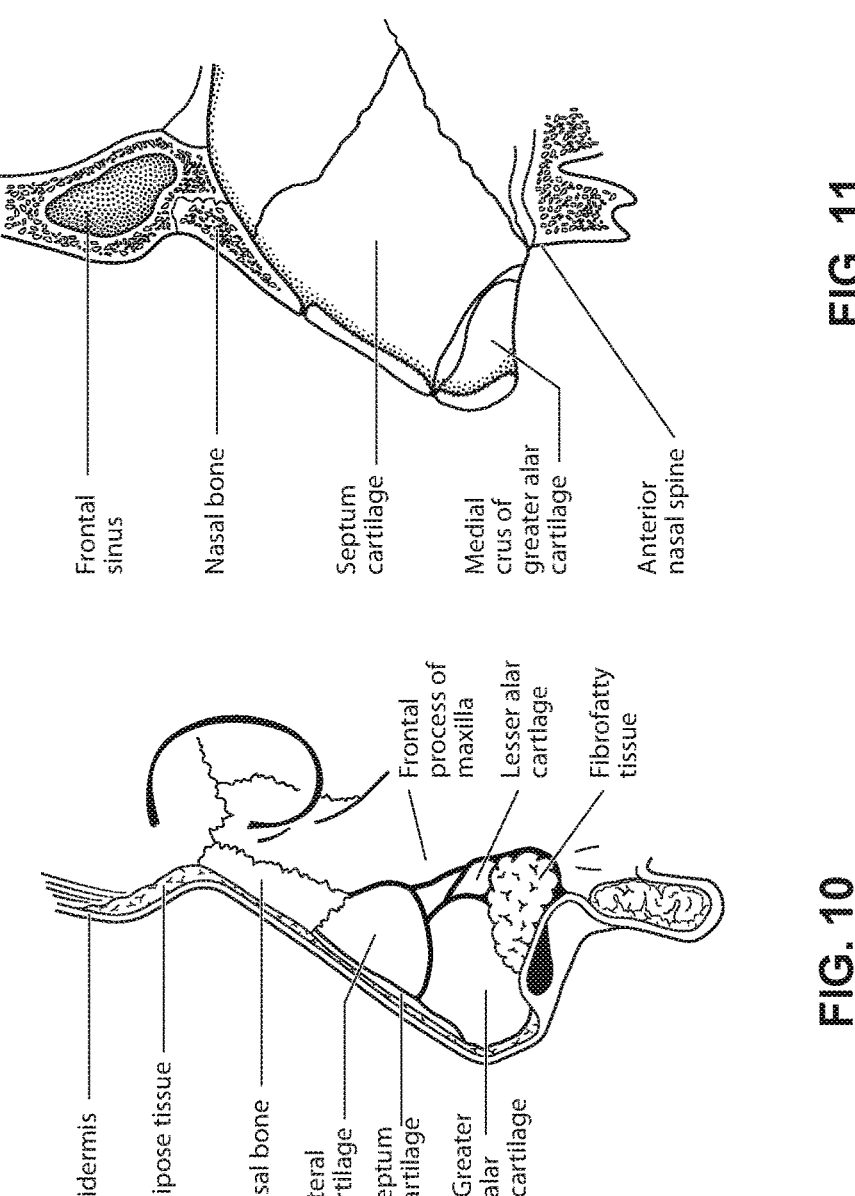
Frontal
sinus
Nasal bone
Septum
cartilage
Medial
crus of
greater alar
cartilage
Anterior
nasal spine
FIG. 11
Frontal
process of
maxilla
Lesser alar
cartilage
Fibrofatty
tissue
Epidermis
Adipose tissue
Nasal bone
Lateral
cartilage
Septum
cartilage
Greater
alar
cartilage
FIG. 10
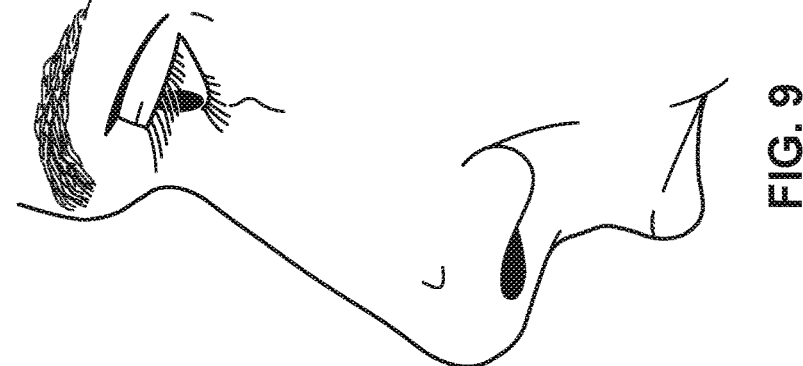
FIG. 9

Frontal bone

Supraorbital foramen

Nasal bones

Septal cartilage

Lateral cartilage

Sesamoid cartilage

Greater alar cartilage

Medial crus of greater alar cartilage

Anterior nasal spine

Infraorbital foramen

Lesser nasal cartilage

Alar fibrofatty tissue

Septal cartilage

Nose - Anterolateral view

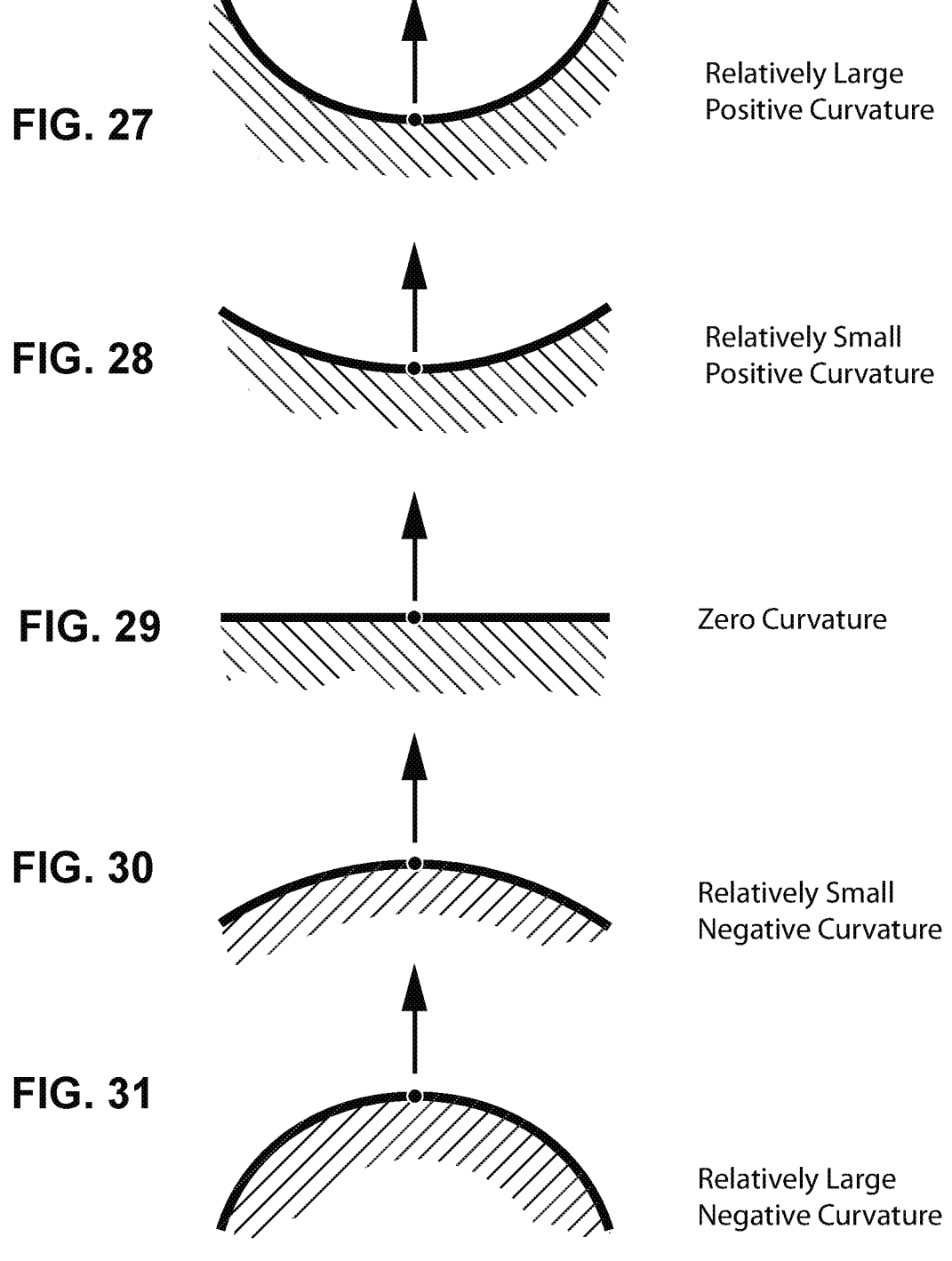
FIG. 27          Relatively Large Positive Curvature
FIG. 28          Relatively Small Positive Curvature
FIG. 29          Zero Curvature
FIG. 30          Relatively Small Negative Curvature
FIG. 31          Relatively Large Negative Curvature

Left-hand rule

Binormal(B)

Osculating plane

Tangent(T)

Normal(N)

Right-hand rule

Binormal(B)

Osculating plane

Tangent(T)

Normal(N)

Left ear helix

T2

B

B

T

N        N

T

T1

**Right-hand helix
Right-hand positive**

Right ear helix

Right-hand negative
(=left-hand positive)

Right-hand positive

Right-hand negative

Right-hand positive

Mid-contact Plane

Sagittal Plane

3200

Mid-Contact Plane          48          Sagittal Plane

3200

48

Sagittal Plane          Mid-Contact Plane 3210          3200

3220

3230

Mid-Contact Plane

3220

3230

PATIENT INTERFACE WITH FOAM CUSHION

This application is the U.S. national phase of International Application No. PCT/IB2019/061217 filed Dec. 20, 2019 which designated the U.S., the entire contents of which are hereby incorporated by reference.

1 BACKGROUND OF THE TECHNOLOGY

1.1 Field of the Technology

The present technology relates to one or more of the screening, diagnosis, monitoring, treatment, prevention and amelioration of respiratory-related disorders. The present technology also relates to medical devices or apparatus, and their use.

1.2 Description of the Related Art 1.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled zi into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchairbound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/ or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

1.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

1.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

1.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched gas at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

1.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

1.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

1.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063, 328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

1.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

1.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH₂O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make Design criteria often conflict, meaning that certain design choices are far from routine or inevitable. Furthermore, the comfort and efficacy of certain aspects may be highly sensitive to small, subtle changes in one or more parameters.

1.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

1.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. Humidifiers therefore often have the capacity to heat the flow of air was well as humidifying it.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

1.2.3.5 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH₂O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(*) one specimen only, measured using test method specified in ISO 3744 in CPAP mode at 10 cm H₂O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

Another aspect of one form of the present technology is directed to a patient interface that may comprise: a plenum chamber; a seal-forming structure; and a positioning and stabilising structure. The patient interface may further comprise a vent structure. The patient interface may further be configured to leave the patient's mouth uncovered, or if the seal-forming structure is configured to seal around the patient's nose and mouth, the patient interface may be further configured to allow the patient to breath from ambient in the absence of a flow of pressurised air through the plenum chamber inlet port.

Another aspect of one form of the present technology is directed to a patient interface comprising: a plenum chamber pressurisable to a therapeutic pressure of at least 4 cmH2O above ambient air pressure, said plenum chamber including a plenum chamber inlet port sized and structured to receive a flow of air at the therapeutic pressure for breathing by a patient; a seal-forming structure constructed and arranged to seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; a positioning and stabilising structure configured to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and a vent structure configured to allow a continuous flow of gases exhaled by the patient from an interior of the plenum chamber to ambient, said vent structure being sized and shaped to maintain the therapeutic pressure in the plenum chamber in use; wherein the patient interface is configured to leave the patient's mouth uncovered, or if the seal-forming structure is configured to seal around the patient's nose and mouth, the patient interface is configured to allow the patient to breath from ambient in the absence of a flow of pressurised air through the plenum chamber inlet port.

Another aspect of one form of the present technology is directed to a patient interface that may comprise: an elastomeric support wall, an elastomeric flange at the end of the elastomeric support wall, and a foam cushion mounted on the elastomeric support flange.

Another aspect of the present technology may be directed to a patient interface configured to deliver a flow of positive pressure respiratory gas to an entrance of a patient's airways including at least an entrance of the patient's nares, the patient interface being configured to maintain a therapy pressure in a range of about 4 cmH2O to about 30 cmH2O above ambient pressure in use, throughout the patient's respiratory cycle, while the patient is sleeping, to ameliorate sleep disordered breathing. The patient interface may include an elastomeric support wall forming at least part of a plenum chamber configured to receive the flow of positive pressure respiratory gas. The patient interface may also include an elastomeric support flange positioned at an end of the elastomeric support wall and extending radially inward from the support wall, the support flange comprising a flap portion at a central superior region of the support flange that extends further in the radially inward direction than the rest of the support flange. A foam cushion may be mounted on the support flange, the foam cushion being configured to form a seal with the patient's face and comprising an attachment surface that is in contact with an outer surface of the support flange.

In further examples of any of the aspects of the preceding paragraphs: (a) the foam cushion may have an attachment surface that is in contact with an outer surface of the support flange, the attachment surface of the foam cushion being widest at a location corresponding to the flap portion, (b) the outer surface of the support flange at the flap portion may have a positive curvature, (c) the central inferior region of the support flange may have a positive curvature, (d) the curvature of the support flange in the flap portion may be larger than the curvature of the support flange in the central inferior region, (e) the central inferior region of the support flange may be between a first pair of negative curvature regions of the support flange, (f) the flap portion may be between a second pair of negative curvature regions of the support flange (g) the support flange may comprise eight transition regions in which the curvature of the outer surface of the support flange transitions from positive to negative or negative to positive, (h) the foam cushion may comprise a sealing surface configured to be in contact with the patient's face in use, (i) the sealing surface of the foam cushion may have a positive curvature at locations where the outer surface of the support flange has a positive curvature, (j) the sealing surface of the foam cushion may have a negative curvature at locations where the outer surface of the support flange has a negative curvature, (k) the outer surface of the support flange in the flap portion may have a saddle shape, (l) the outer surface of the support flange in the central inferior region may have a saddle shape, (m) the outer surface of the support flange in the flap portion may be between a first pair of dome regions, (n) the outer surface of the support flange in the central inferior region may be between a second pair of dome regions, (o) the foam cushion may overhang the support flange, (p) the patient interface may further comprise a shell with an inlet opening configured to receive the flow of positive pressure respiratory gas, (q) the support wall may be mounted to the shell, (r) the patient interface may further comprise a positioning and stabilizing structure configured to support the shell, the support wall, and the foam cushion on the patient's head, (s) the positioning and stabilizing structure may be removably attachable to the shell, (t) the positioning and stabilizing structure may comprise a shroud and a plurality of headgear straps, (u) the shroud may be removably attachable to the shell at the inlet opening, and/or (v) the patient interface may further comprise an air delivery tube connectable to the shroud and the shell.

Another aspect of the present technology may be directed to a patient interface configured to deliver a flow of positive pressure respiratory gas to an entrance of a patient's airways including at least an entrance of the patient's nares, the patient interface being configured to maintain a therapy pressure in a range of about 4 cmH2O to about 30 cmH2O above ambient pressure in use, throughout the patient's respiratory cycle, while the patient is sleeping, to ameliorate sleep disordered breathing. The patient interface may include an elastomeric support wall forming at least part of a plenum chamber configured to receive the flow of positive pressure respiratory gas. The patient interface may also include an elastomeric support flange positioned at an end of the elastomeric support wall and extending radially inward from the support wall. A foam cushion may be mounted on the support flange, the foam cushion being configured to form a seal with the patient's face. An elastomeric wall thickness of the support flange may vary from a central superior region of the support flange to a central inferior region of the support flange.

In further examples of any of the aspects of the preceding paragraph: (a) the elastomeric wall thickness of the support flange may be thinner at the central superior region and the central inferior region than in intermediate regions between the central superior region and the central inferior region, (b) the elastomeric wall thickness of the support flange may be thinner at the central superior region than at the central inferior region, (c) an elastomeric wall thickness of the support wall may vary from a central superior region of the support wall to a central inferior region of the support wall, (d) the elastomeric wall thickness of the support wall may be thinner at the central superior region of the support wall and at the central inferior region of the support wall than at the intermediate regions between the central superior region and the central inferior region, (e) the elastomeric wall thickness of the support wall may be thinner at the central superior region than at the central inferior region, (f) the central superior region of the support wall may comprise a superior gusset, (g) the central inferior region of the support wall may comprise an inferior gusset, (g) the inferior gusset may be more collapsible than the superior gusset (h) a thickness of the foam cushion may be consistent throughout the foam cushion, (i) the patient interface may further comprise a pair of compressible ribs at an inferior region of the patient interface, (j) each of the compressible ribs may be attached to the support wall and the support flange and may be configured to prevent at least a portion of the support flange from flexing due to positive pressure in the plenum chamber, (k) the support flange may comprise a flap portion at the central superior region of the support flange that extends further in the radially inward direction than the rest of the support flange, (l) the flap portion may be configured to prevent at least a portion of the support flange from flexing due to positive pressure in the plenum chamber, (m) the foam cushion may overhang the support flange, (n) the patient interface may further comprise a shell with an inlet opening configured to receive the flow of positive pressure respiratory gas, (o) the support wall may be mounted to the shell, (p) the patient interface may further comprise a positioning and stabilizing structure configured to support the shell, the support wall, and the foam cushion on the patient's head, (q) the positioning and stabilizing structure may be removably attachable to the shell, (r) the positioning and stabilizing structure may comprise a shroud and a plurality of headgear straps, (s) the shroud may be removably attachable to the shell at the inlet opening, (t) the patient interface may further comprise an air delivery tube connectable to the shroud and the shell.

Another aspect of the present technology is directed to a patient interface that may comprise: a shell with an inlet opening configured to receive a flow of respiratory gas, a support wall mounted on the shell, a support flange positioned at an end of the support wall, and a foam cushion mounted on the support flange.

Another aspect of the present technology may be directed to a patient interface configured to deliver a flow of positive pressure respiratory gas to an entrance of a patient's airways including at least an entrance of the patient's nares, the patient interface being configured to maintain a therapy pressure in a range of about 4 cmH2O to about 30 cmH2O above ambient pressure in use, throughout the patient's respiratory cycle, while the patient is sleeping, to ameliorate sleep disordered breathing. The patient interface may include a shell with an inlet opening configured to receive the flow of positive pressure respiratory gas. The patient interface may also include an elastomeric support wall mounted to the shell. The shell and the elastomeric support wall may together form at least part of a plenum chamber configured to receive the flow of positive pressure respiratory gas. An elastomeric support flange may be positioned at an end of the elastomeric support wall and may extend radially inward from the support wall. A foam cushion may be mounted on the support flange. The foam cushion may be configured to form a seal with the patient's face. The elastomeric support wall and the foam cushion may be configured so that when the patient interface is mounted on the patient's face, the part of the central longitudinal axis of the inlet opening that is outside of the patient interface extends at least partly in an inferior direction.

In further examples of any of the aspects of the preceding paragraphs: (a) the support wall may be configured to pivot around a lateral axis that extends through lateral sides of the support wall, (b) the support wall may be configured so that when the support wall pivots from a neutral position, the inlet opening of the shell rotates so that the portion of the central longitudinal axis of the inlet opening outside of the patient interface rotates toward the inferior direction, (c) an inferior portion of the support wall may comprise an inferior gusset, (d) the inferior gusset may be configured so that the support wall pivots around the lateral axis when the inferior gusset is collapsed, (e) a superior portion of the support wall may comprise a superior gusset (f) the patient interface may further comprise a positioning and stabilizing structure configured to support the shell, the support wall, and the foam cushion on the patient's head, (g) the positioning and stabilizing structure may be removably attachable to the shell, (h) the positioning and stabilizing structure may comprise a shroud and a plurality of headgear straps, (i) the shroud may be removably attachable to the shell at the inlet opening, and/or (j) the patient interface may further comprise an air delivery tube connectable to the shroud and the shell.

Another aspect of the present technology may be directed to a patient interface configured to deliver a flow of positive pressure respiratory gas to an entrance of a patient's airways including at least an entrance of the patient's nares, the patient interface being configured to maintain a therapy pressure in a range of about 4 cmH2O to about 30 cmH2O above ambient pressure in use, throughout the patient's respiratory cycle, while the patient is sleeping, to ameliorate sleep disordered breathing. The patient interface may include an elastomeric support wall forming at least part of a plenum chamber configured to receive the flow of positive pressure respiratory gas. The patient interface may further include an elastomeric support flange positioned at an end of the elastomeric support wall and extending radially inward from the support wall. A foam cushion may be mounted onto the support flange. The foam cushion may comprise an attachment surface configured to be attached to the support flange and may comprise a sealing surface configured to contact and form a seal with the patient's face. The foam cushion may be bent around a bisecting plane that bisects the foam cushion and extends through a central superior region and a central inferior region of the foam cushion. The attachment surface and the sealing surface may be wider at the bisecting plane than at the remaining portions of the foam cushion.

In further examples of any of the aspects of the preceding paragraph: (a) the foam cushion may comprise a perimeter surface extending from the attachment surface to the sealing surface, (b) the perimeter surface may be concave at the central inferior region, (c) the attachment surface and the sealing surface may have the same width over the entirety of the foam cushion, (d) the foam cushion may overhang the support flange by the same amount over the entirety of the foam cushion, (e) the patient interface may comprise a shell with an inlet opening configured to receive the flow of positive pressure respiratory gas, (f) the support wall may be mounted to the shell, (g) the patient interface may further comprise a positioning and stabilizing structure configured to support the shell, the support wall, and the foam cushion on the patient's head, (h) the positioning and stabilizing structure may be removably attachable to the shell, (i) the positioning and stabilizing structure may comprise a shroud and a plurality of headgear straps, (j) the shroud may be removably attachable to the shell at the inlet opening, and/or (k) the patient interface may further comprise an air delivery tube connectable to the shroud and the shell.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Respiratory Therapy Systems

FIG. 1 shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 2 shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

3.2 Respiratory System and Facial Anatomy

Figure 7:
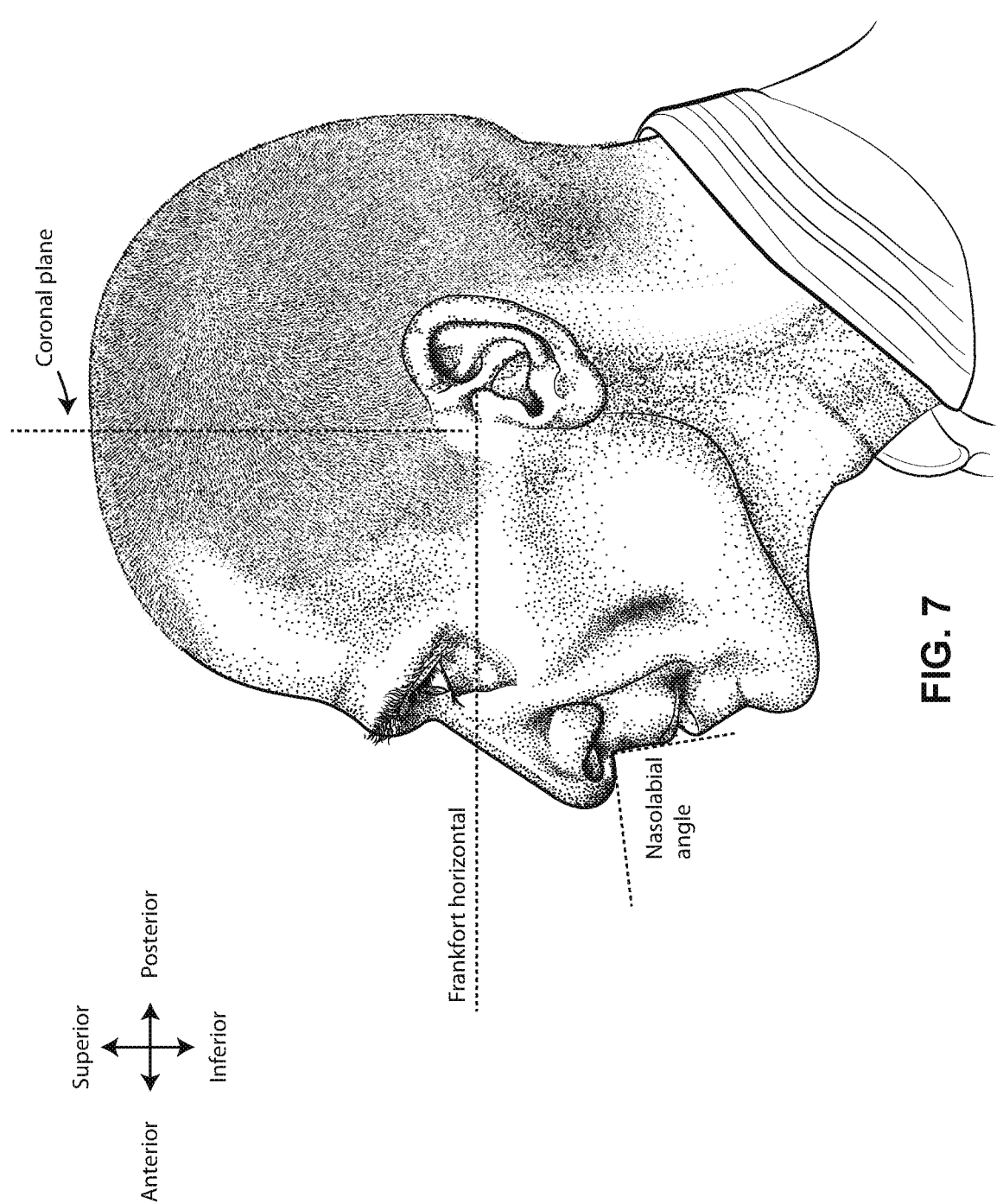

FIG. 7 is a further side view of a head. The approximate locations of the Frankfort horizontal and nasolabial angle are indicated. The coronal plane is also indicated.

Figure 8:
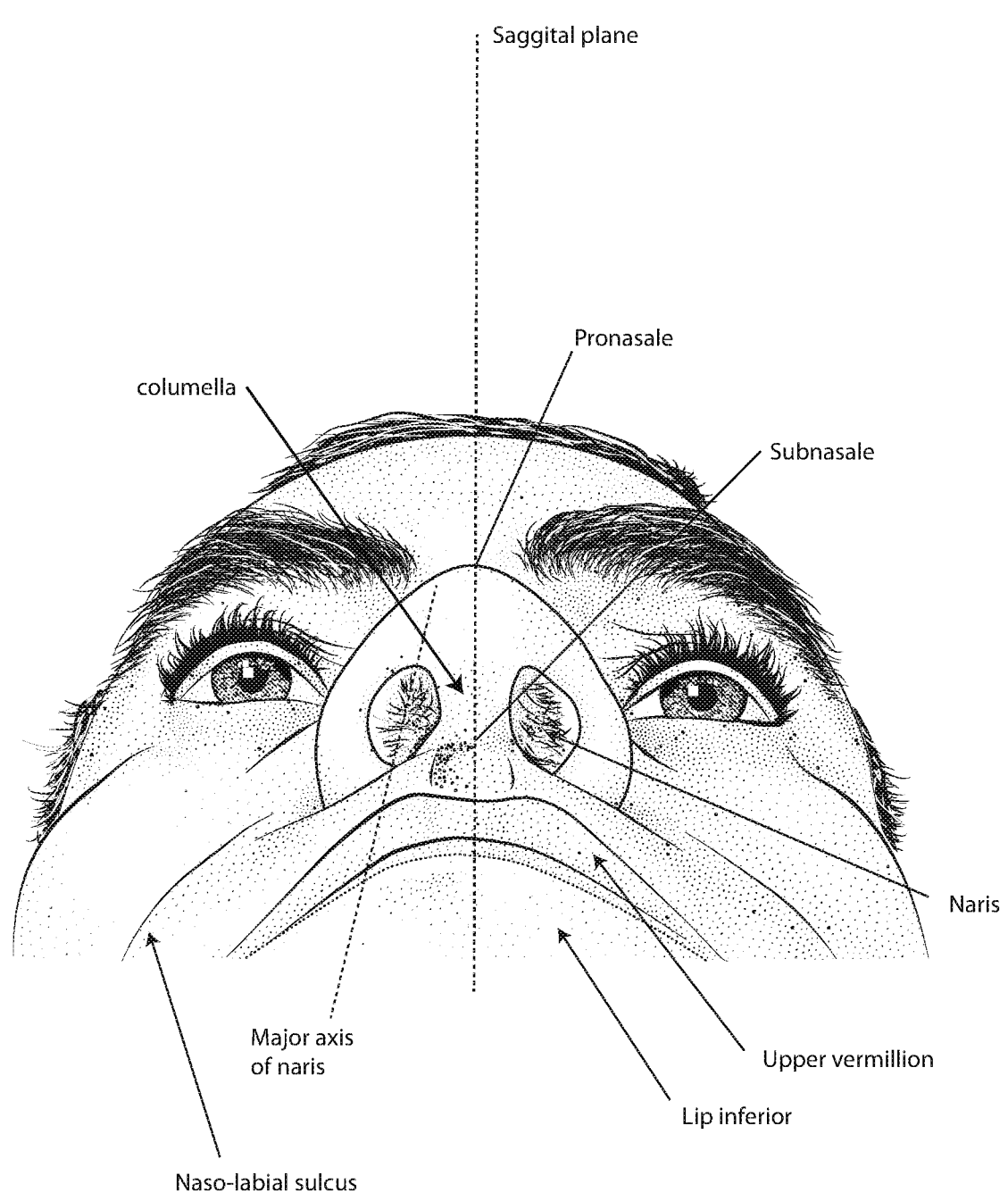

FIG. 8 shows a base view of a nose with several features identified including naso-labial sulcus, lip inferior, upper Vermilion, naris, subnasale, columella, pronasale, the major axis of a naris and the midsagittal plane.

FIG. 9 shows a side view of the superficial features of a nose.

FIG. 10 shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 11 shows a medial dissection of a nose, approximately several millimeters from the midsagittal plane, amongst other things showing the septum cartilage and medial crus of greater alar cartilage.

Figures 12, 13:
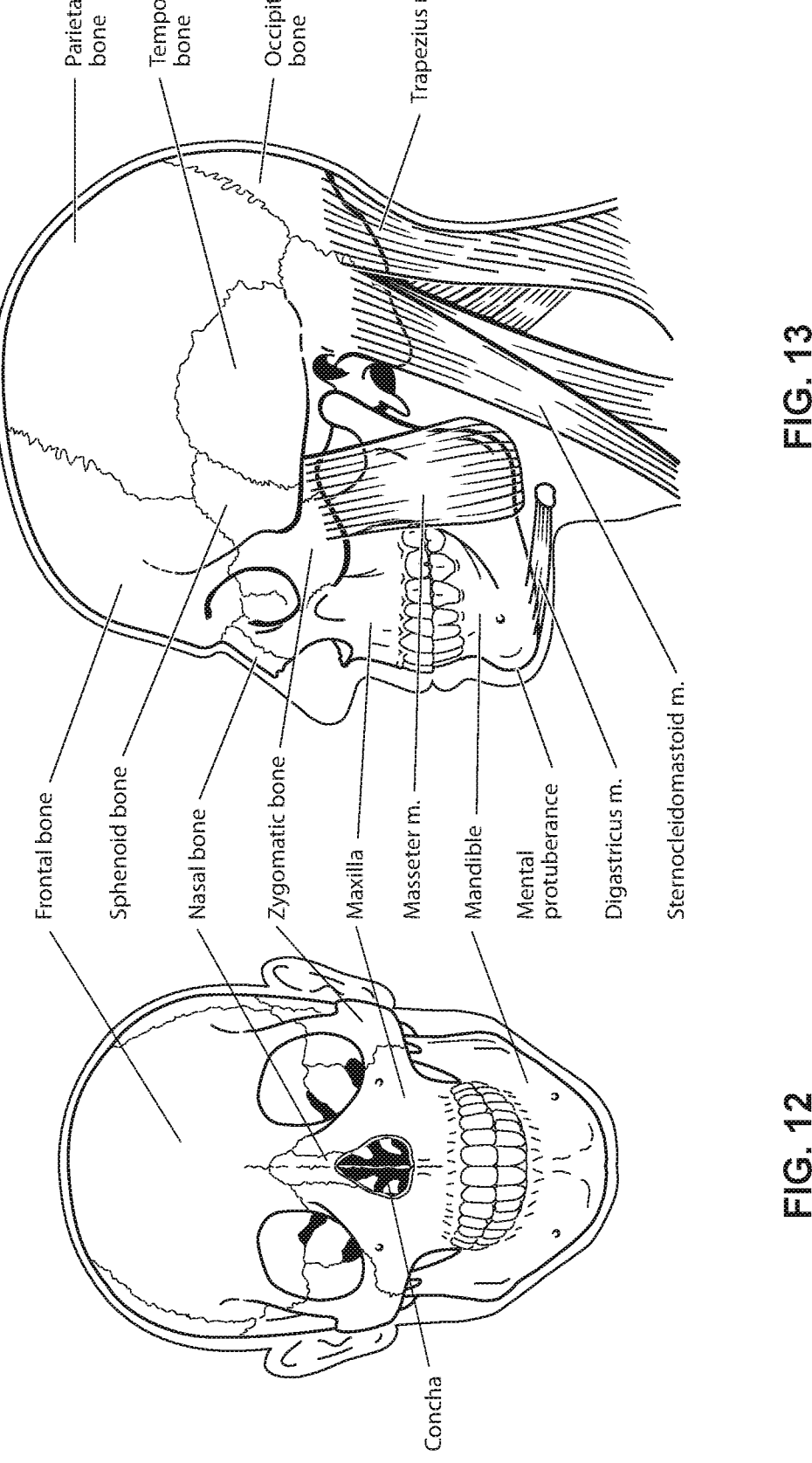

FIG. 12 shows a front view of the bones of a skull including the frontal, nasal and zygomatic bones. Nasal concha are indicated, as are the maxilla, and mandible.

FIG. 13 shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 14:
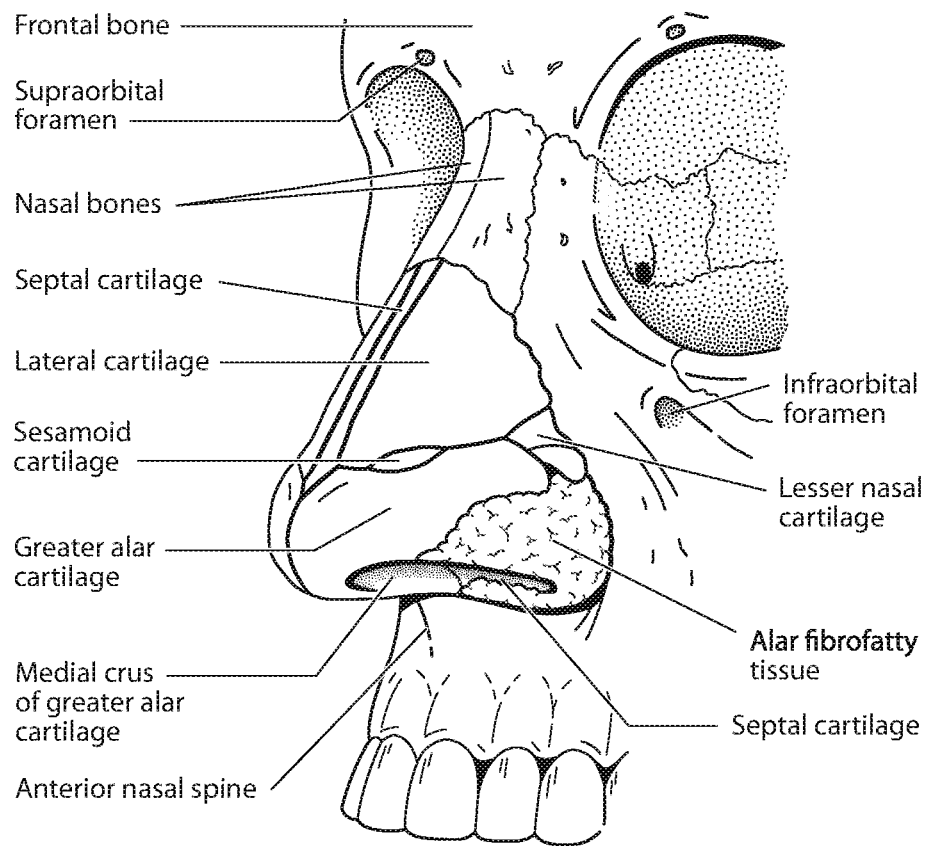

FIG. 14 shows an anterolateral view of a nose.

3.3 Patient Interface

Figure 15:
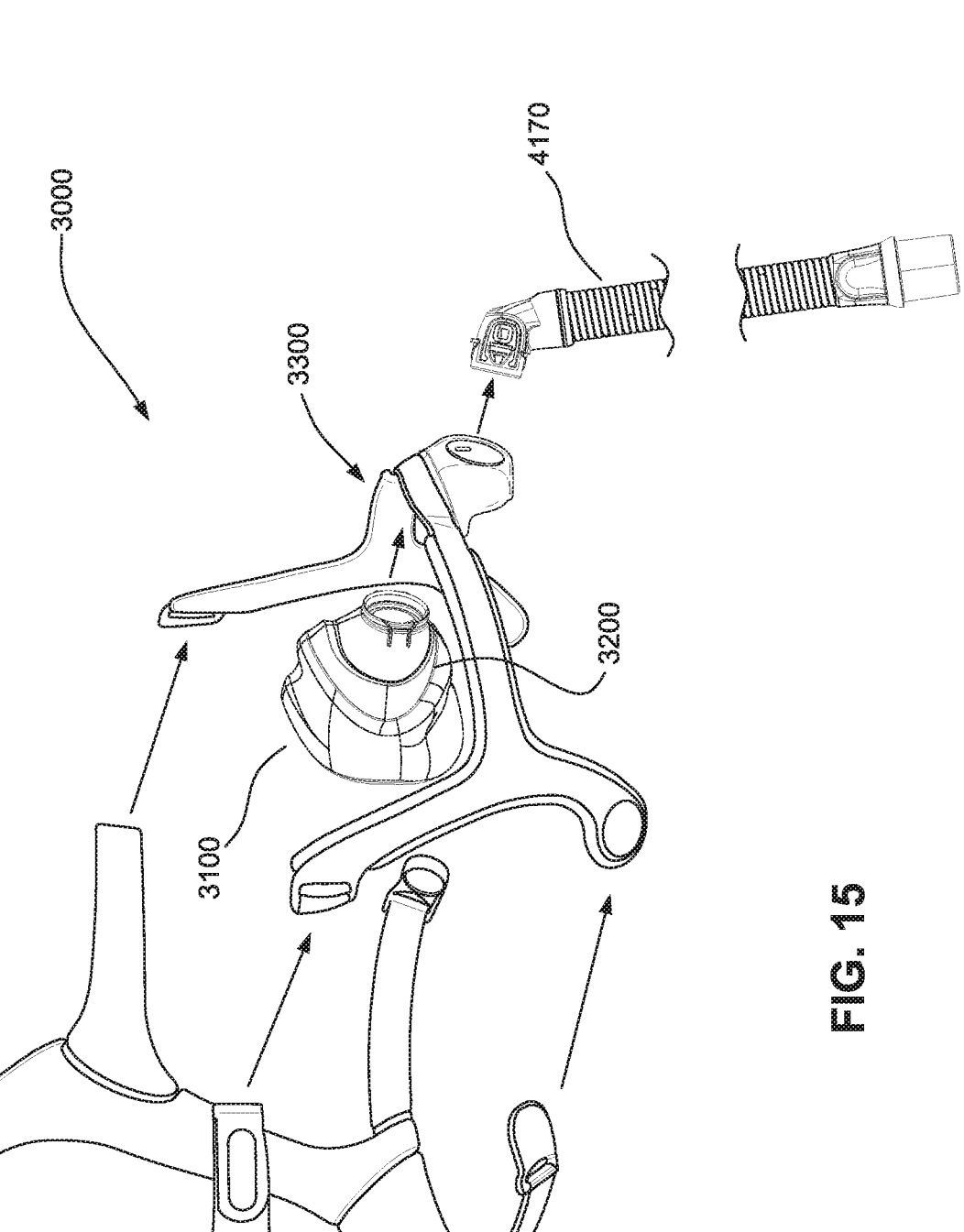

FIG. 15 shows a patient interface in the form of a nasal mask in accordance with one form of the present technology.

Figure 16:
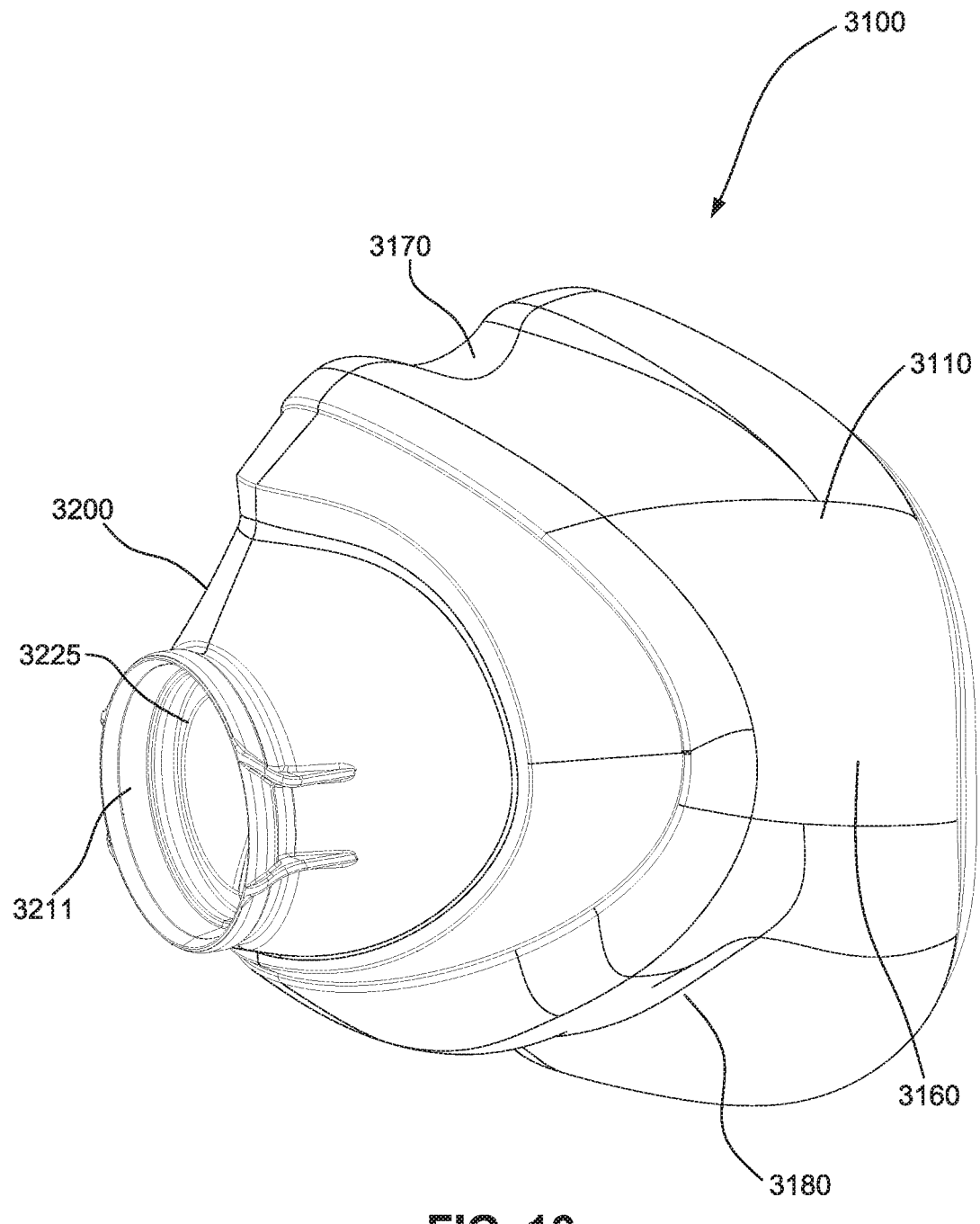

FIG. 16 shows a perspective view of an exemplary patient interface.

Figures 17, 18:
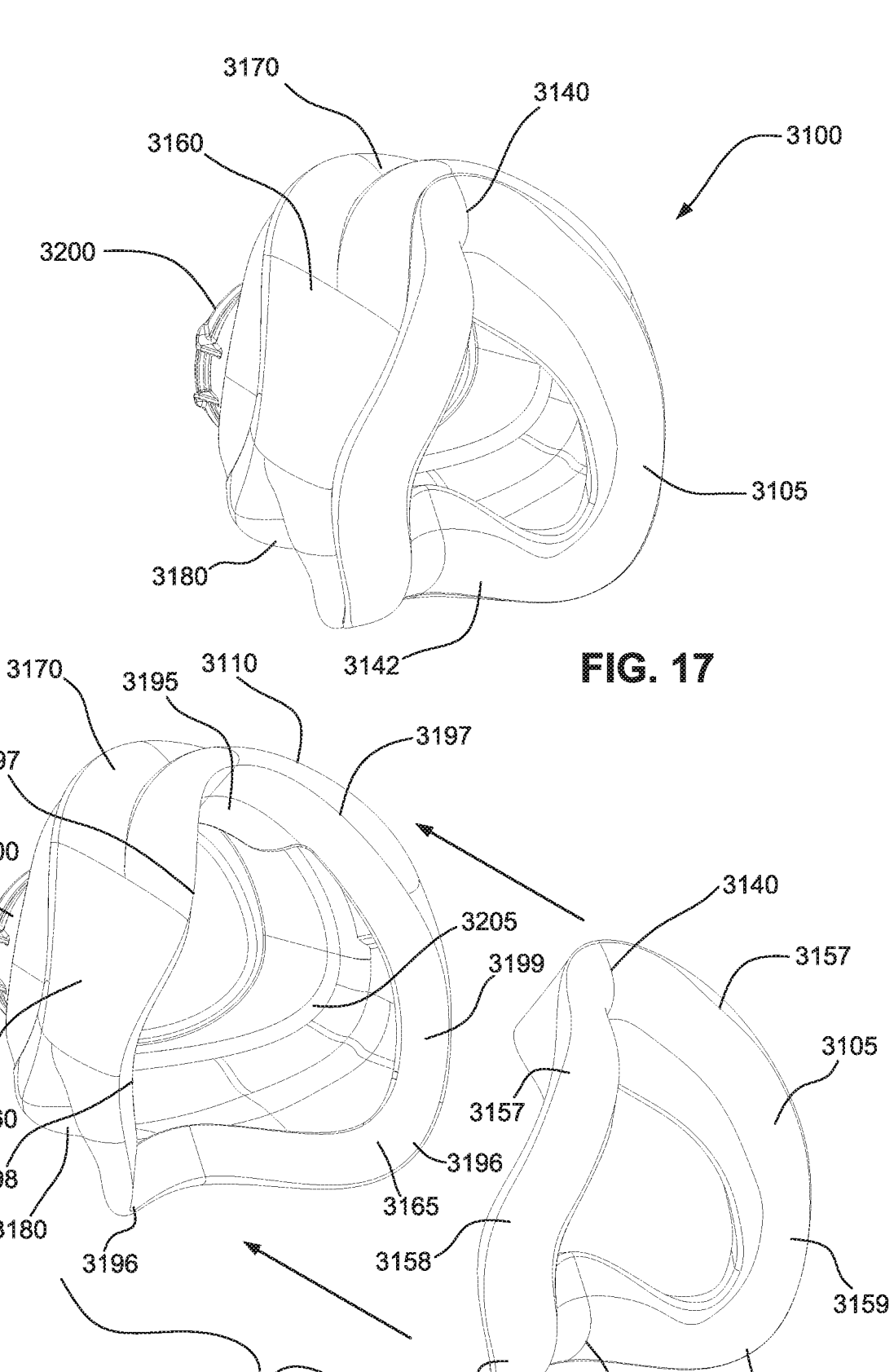

FIG. 17 shows another perspective view of the exemplary patient interface.

FIG. 18 shows an exploded view of the exemplary patient interface.

Figure 19:
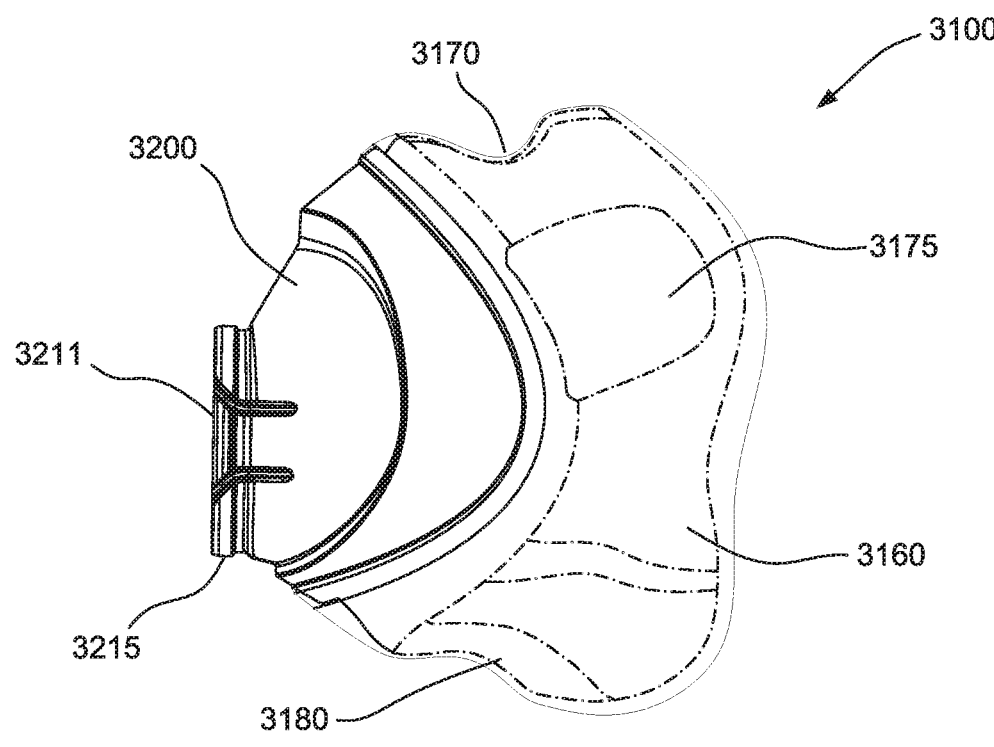
Figure 20:
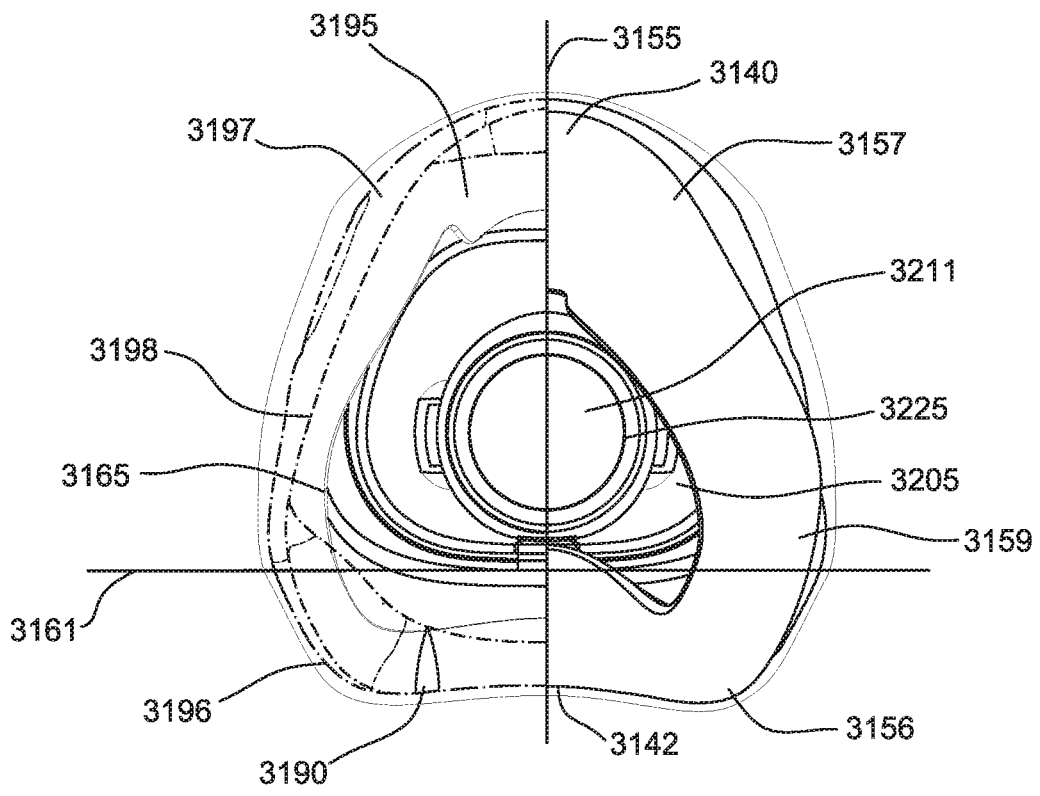

FIG. 19 shows a side view of an exemplary foam cushion,

FIG. 20 shows a rear view of the exemplary patient interface.

Figure 21:
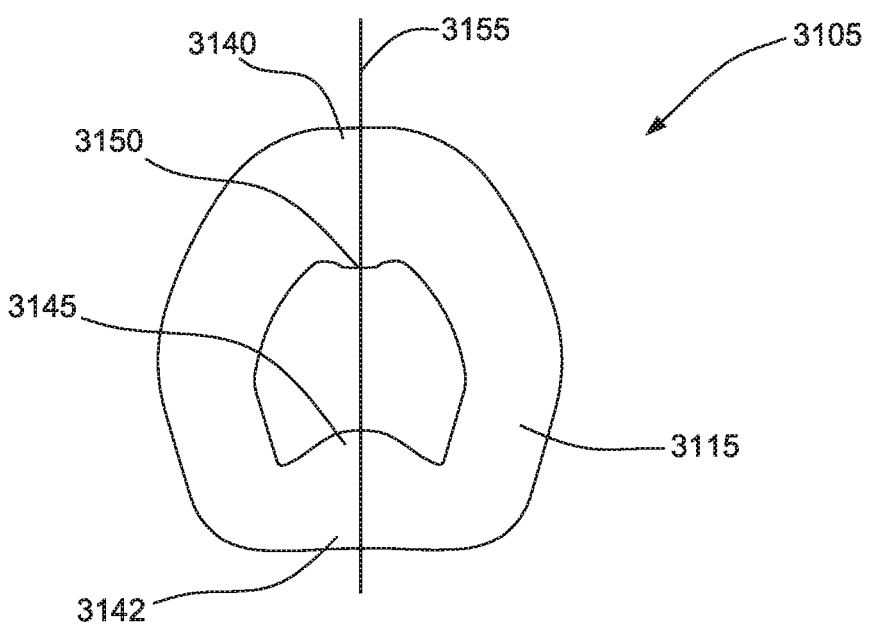

FIG. 21 shows a rear view of the exemplary foam cushion in a mounted state.

Figure 22:
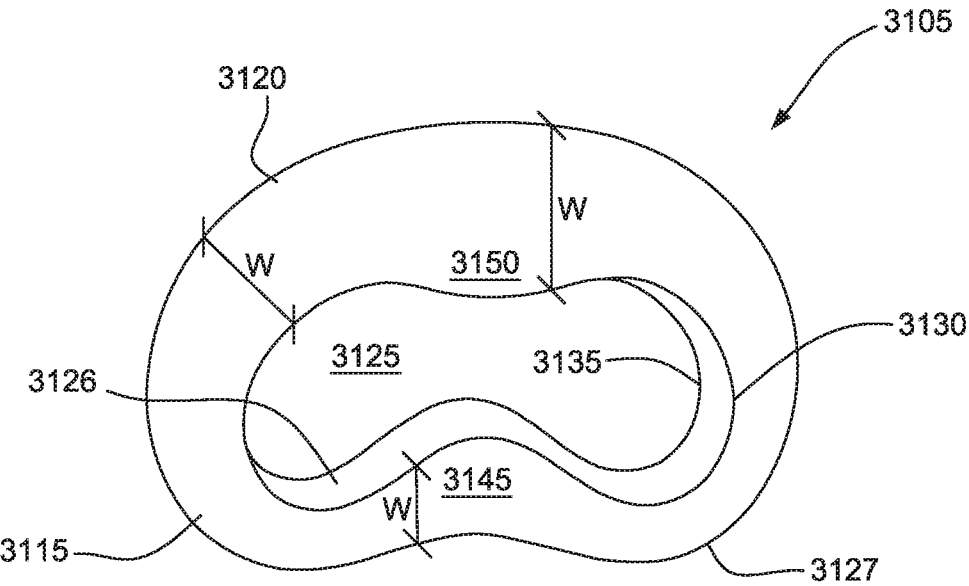

FIG. 22 shows another rear view of the exemplary foam cushion in an unmounted state.

Figure 23:
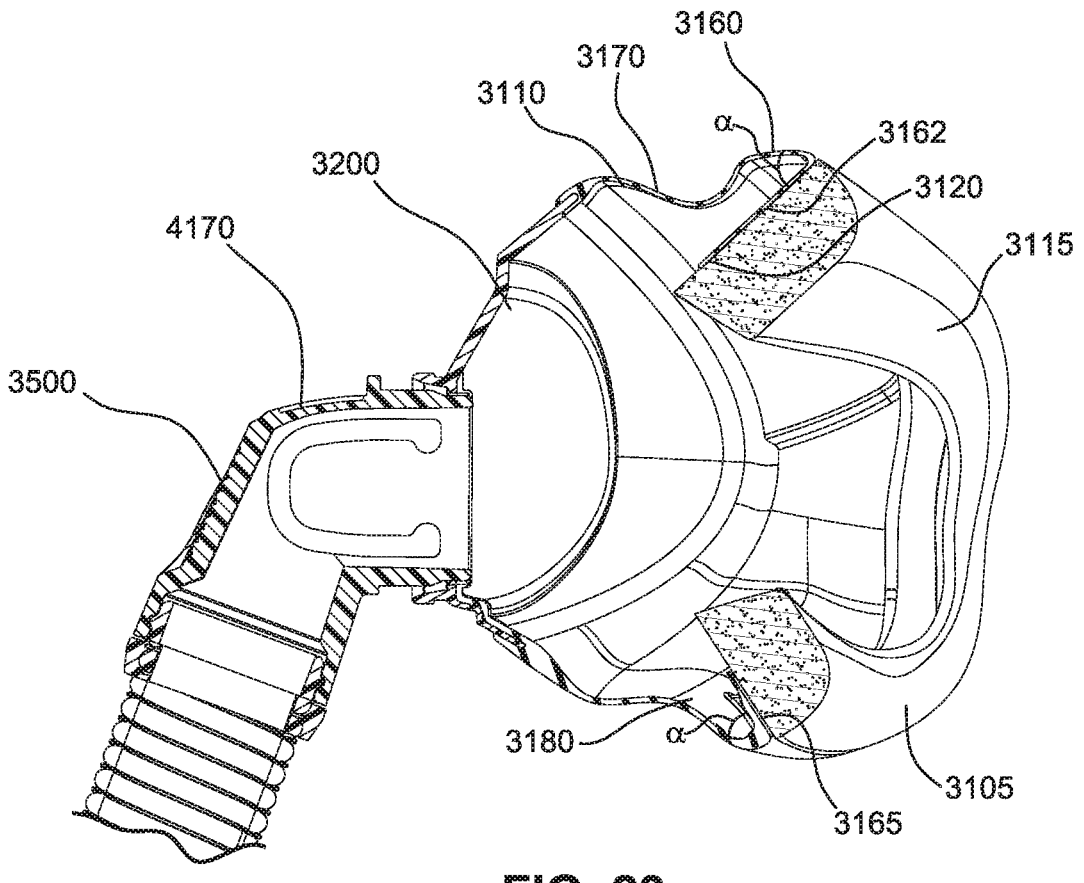

FIG. 23 shows another side view of the exemplary patient interface.

Figure 24:
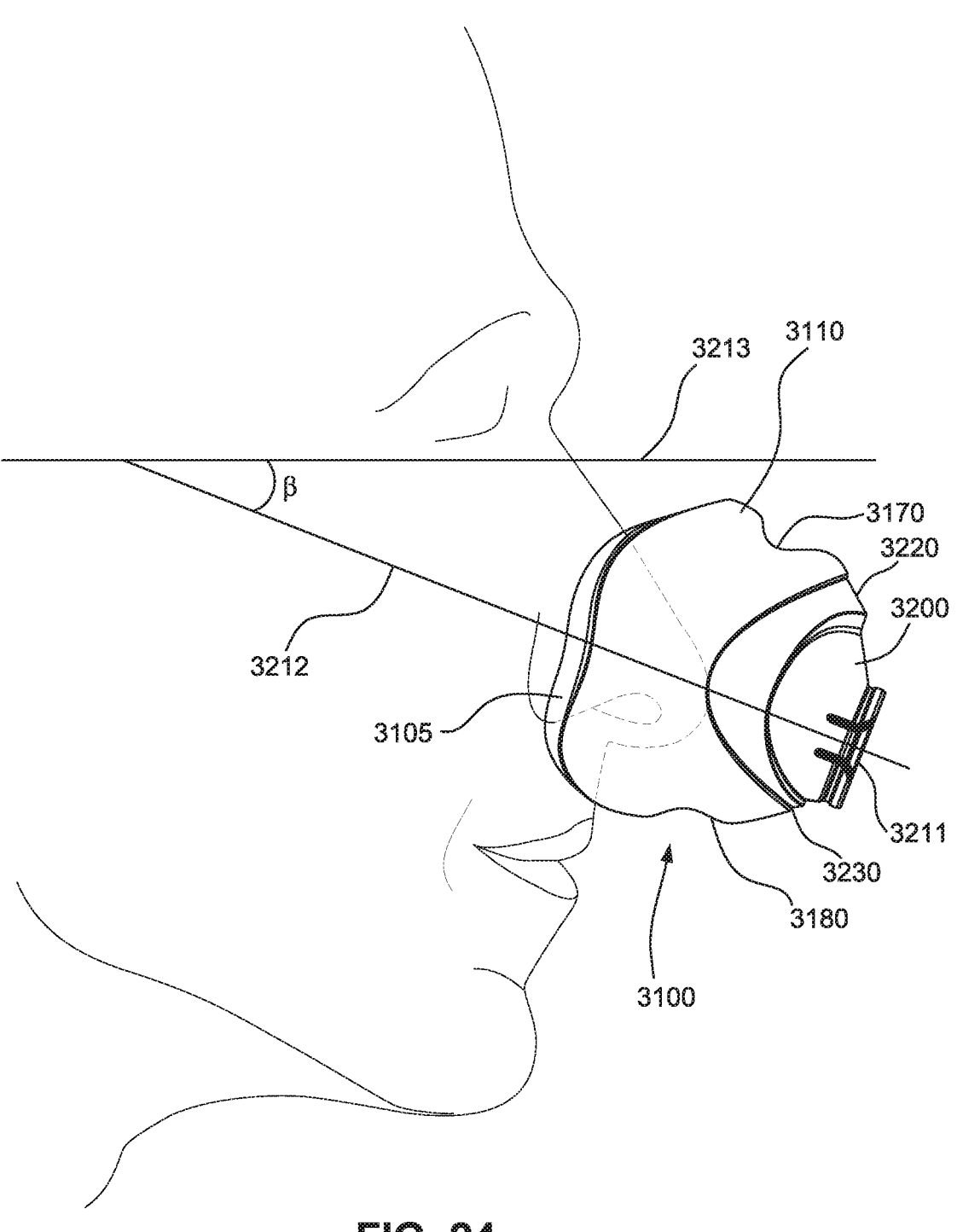

FIG. 24 shows a side view of an exemplary patient interface mounted on a patient's face.

Figure 24A:
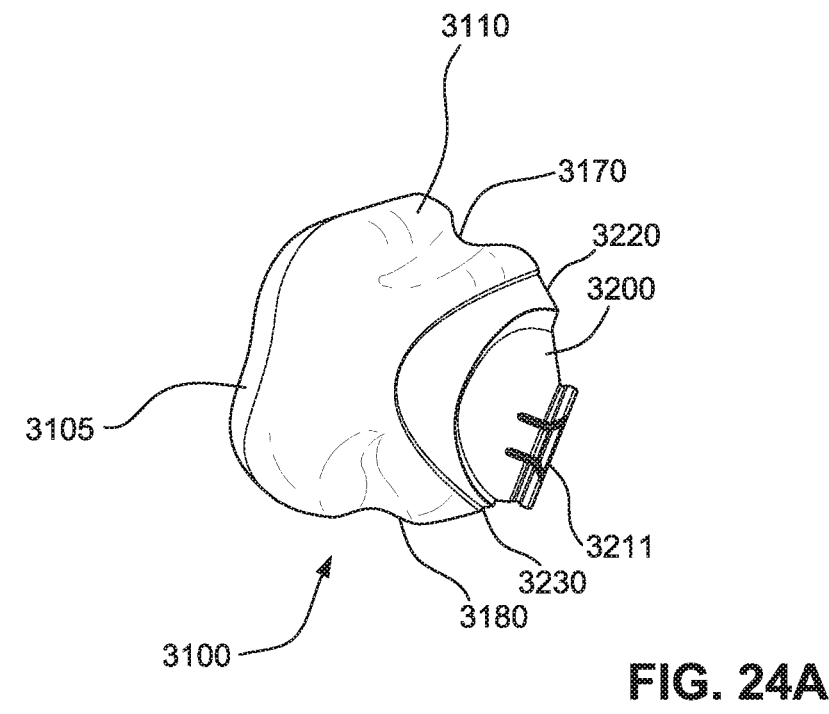

FIG. 24A shows a side view of the patient interface of FIG. 24 without the patient's face.

Figure 24B:
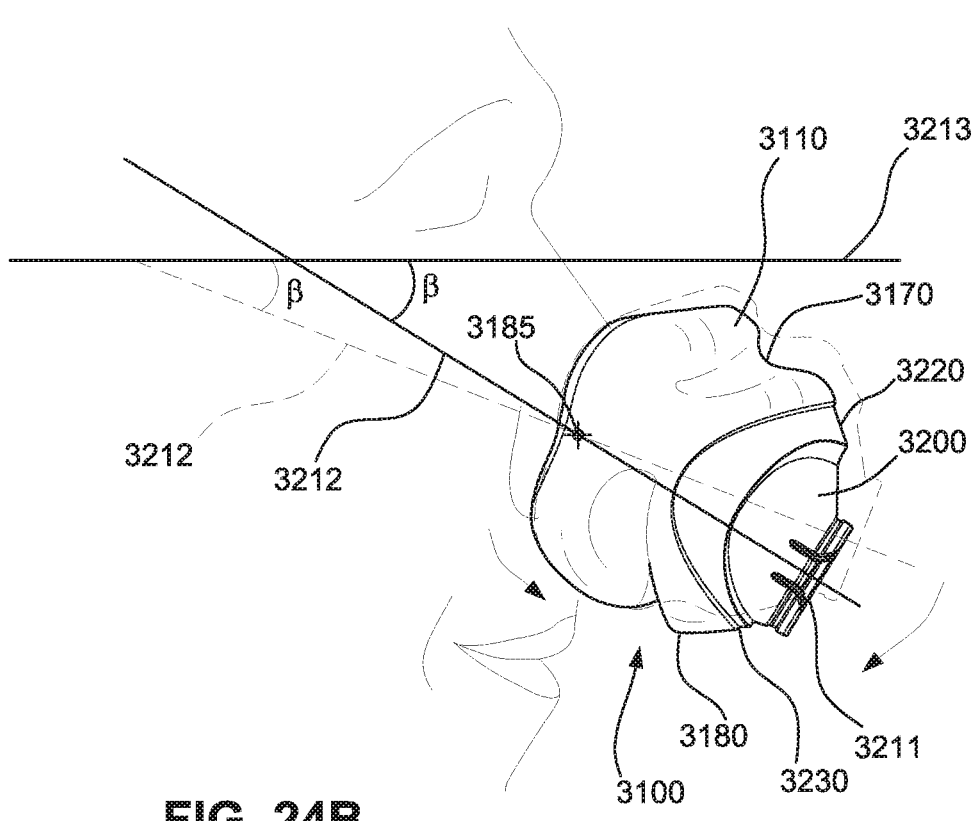

FIG. 24B shows a side view of the patient interface of FIG. 24 when the patient interface is pivoted.

Figure 25:
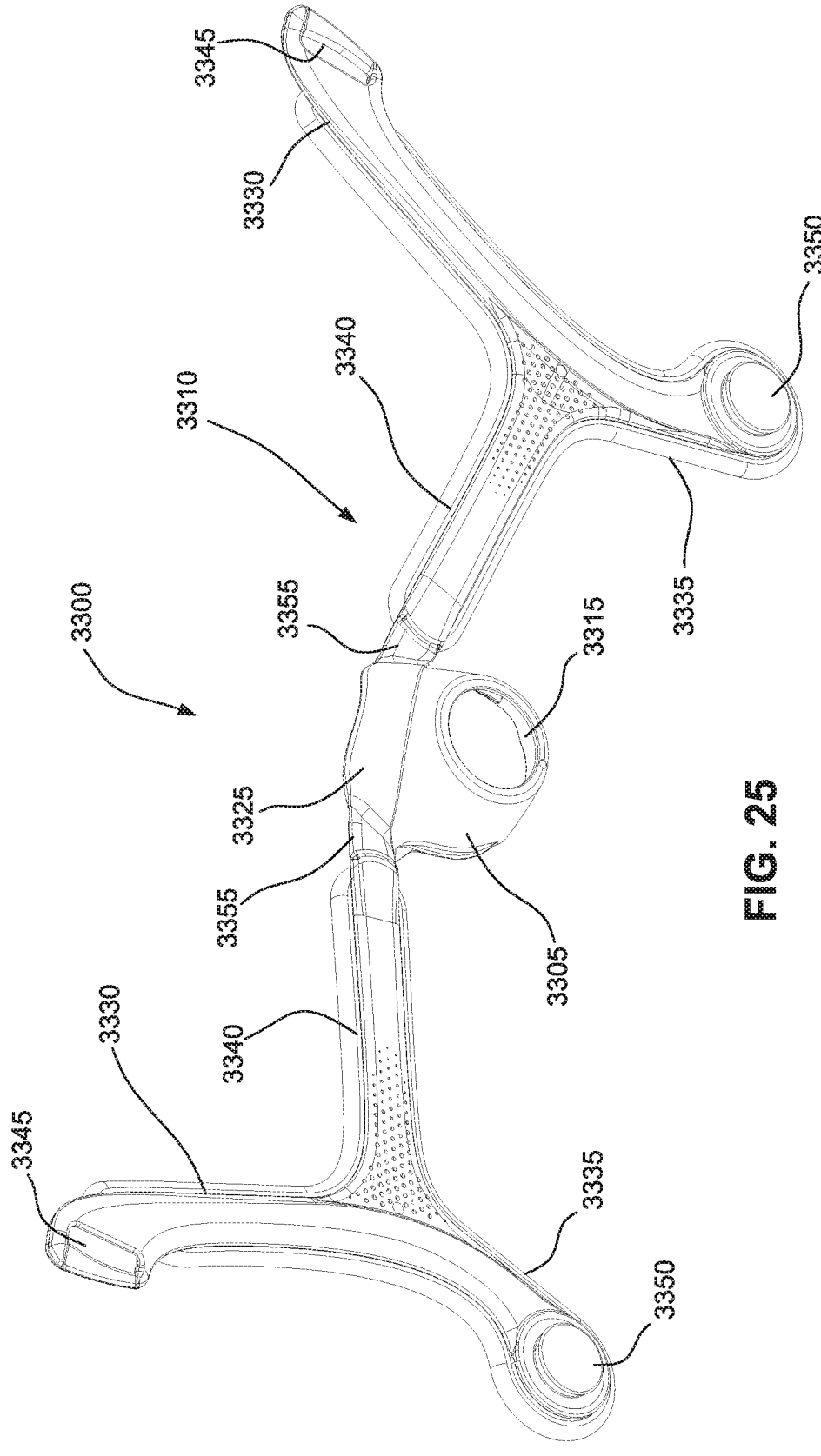

FIG. 25 shows a perspective view of an exemplary frame assembly.

Figure 26:
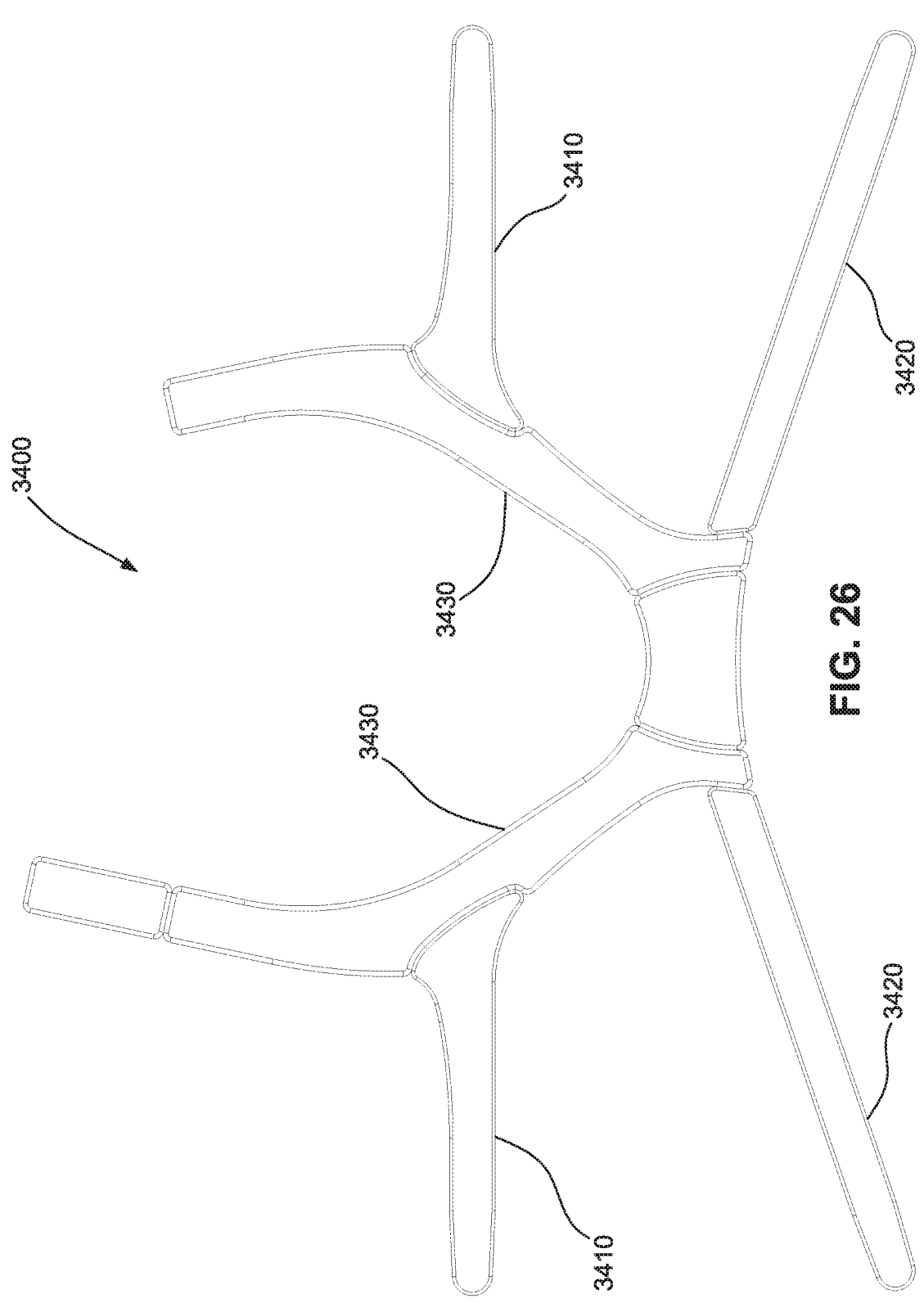

FIG. 26 shows an exemplary positioning and stabilizing system.

3.3.1 Surface Shapes and Reference Points

FIG. 27 shows a schematic of a cross-section through a structure at a point. An outward normal at the point is indicated. The curvature at the point has a positive sign, and a relatively large magnitude when compared to the magnitude of the curvature shown in FIG. 28.

FIG. 28 shows a schematic of a cross-section through a structure at a point. An outward normal at the point is indicated. The curvature at the point has a positive sign, and a relatively small magnitude when compared to the magnitude of the curvature shown in FIG. 27.

FIG. 29 shows a schematic of a cross-section through a structure at a point. An outward normal at the point is indicated. The curvature at the point has a value of zero.

FIG. 30 shows a schematic of a cross-section through a structure at a point. An outward normal at the point is indicated. The curvature at the point has a negative sign, and a relatively small magnitude when compared to the magnitude of the curvature shown in FIG. 31.

FIG. 31 shows a schematic of a cross-section through a structure at a point. An outward normal at the point is indicated. The curvature at the point has a negative sign, and a relatively large magnitude when compared to the magnitude of the curvature shown in FIG. 30.

Figures 32, 33:
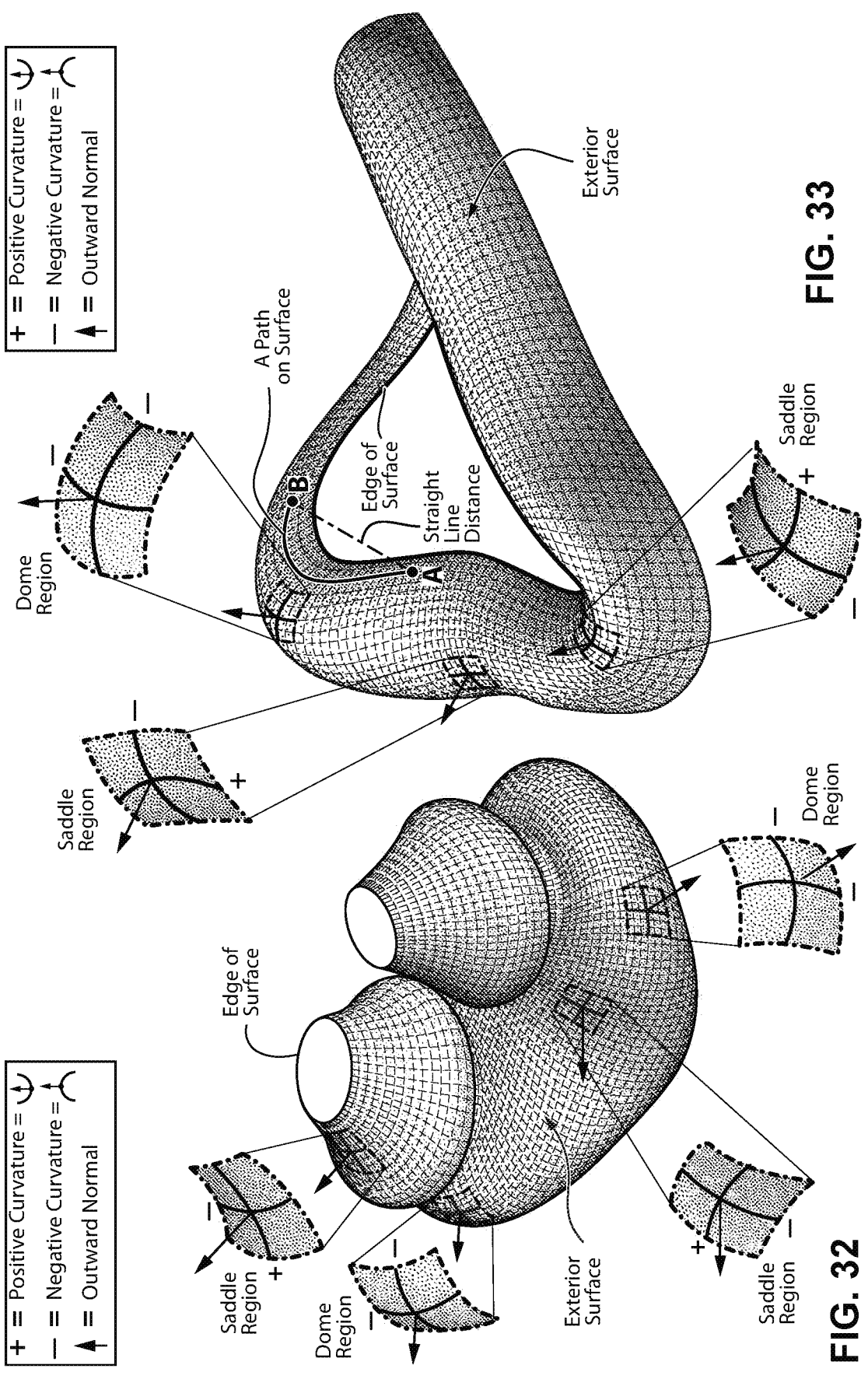

FIG. 32 shows a cushion for a mask that includes two pillows. An exterior surface of the cushion is indicated. An edge of the surface is indicated. Dome and saddle regions are indicated.

FIG. 33 shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figures 34, 35, 36, 37, 38, 39:
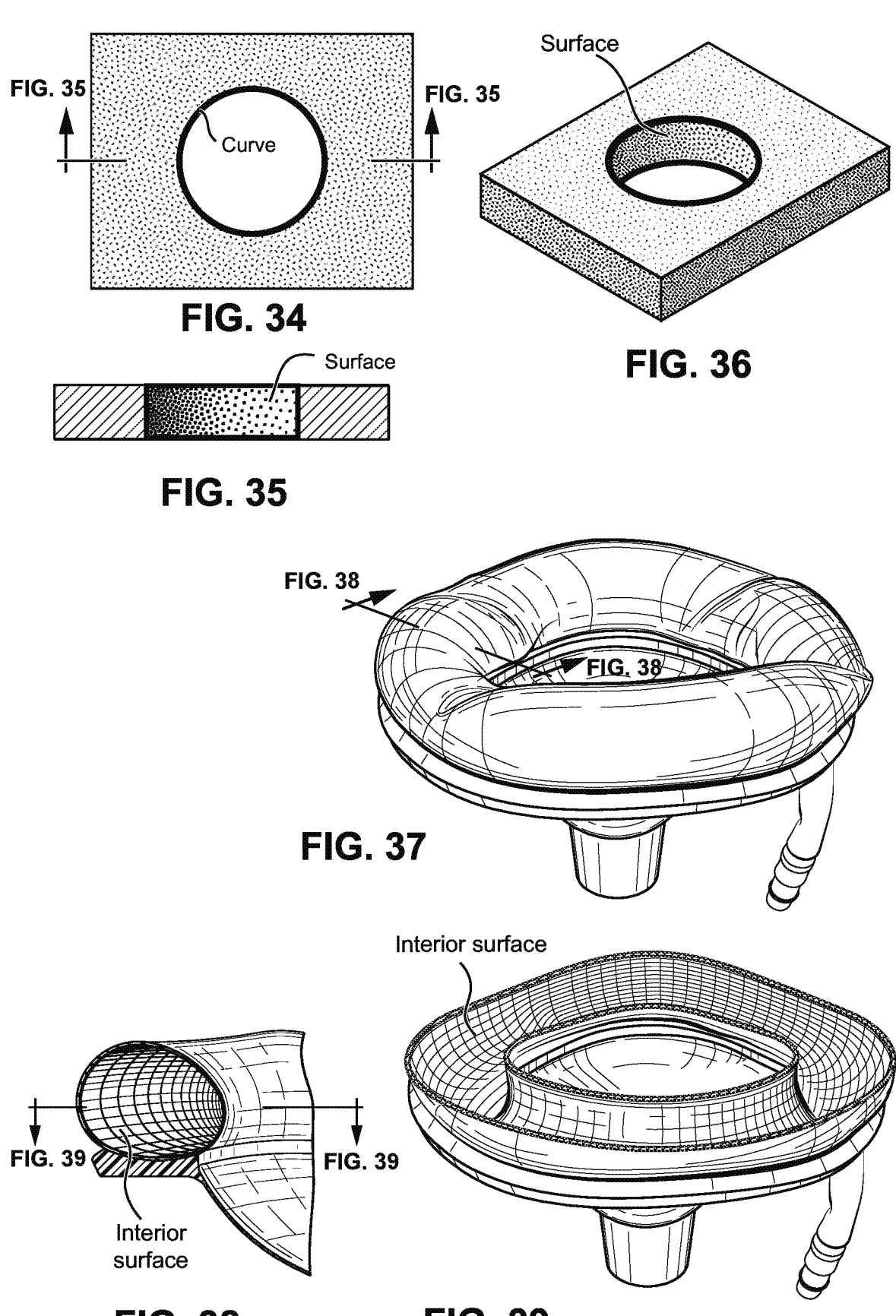

FIG. 34 shows the surface of a structure, with a one dimensional hole in the surface. The illustrated plane curve forms the boundary of a one dimensional hole.

FIG. 35 shows a cross-section through the structure of FIG. 34. The illustrated surface bounds a two dimensional hole in the structure of FIG. 34.

FIG. 35 shows a perspective view of the structure of FIG. 34, including the two dimensional hole and the one dimensional hole. Also shown is the surface that bounds a two dimensional hole in the structure of FIG. 34.

FIG. 37 shows a mask having an inflatable bladder as a cushion.

FIG. 38 shows a cross-section through the mask of FIG. 37, and shows the interior surface of the bladder. The interior surface bounds the two dimensional hole in the mask.

FIG. 39 shows a further cross-section through the mask of FIG. 37. The interior surface is also indicated.

Figures 40, 41, 42, 43, 44, 45:
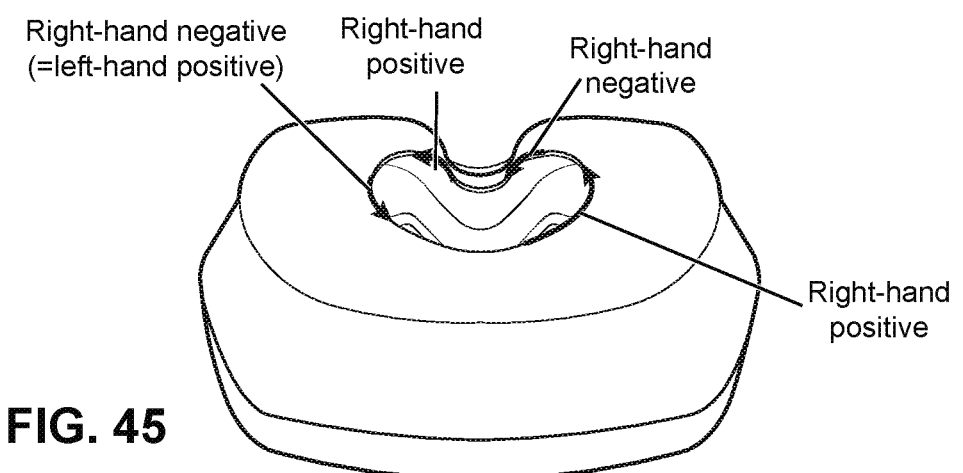

FIG. 40 illustrates a left-hand rule.

FIG. 41 illustrates a right-hand rule.

FIG. 42 shows a left ear, including the left ear helix.

FIG. 43 shows a right ear, including the right ear helix.

FIG. 44 shows a right-hand helix.

FIG. 45 shows a view of a mask, including the sign of the torsion of the space curve defined by the edge of the sealing membrane in different regions of the mask.

Figures 46, 47, 48, 49:
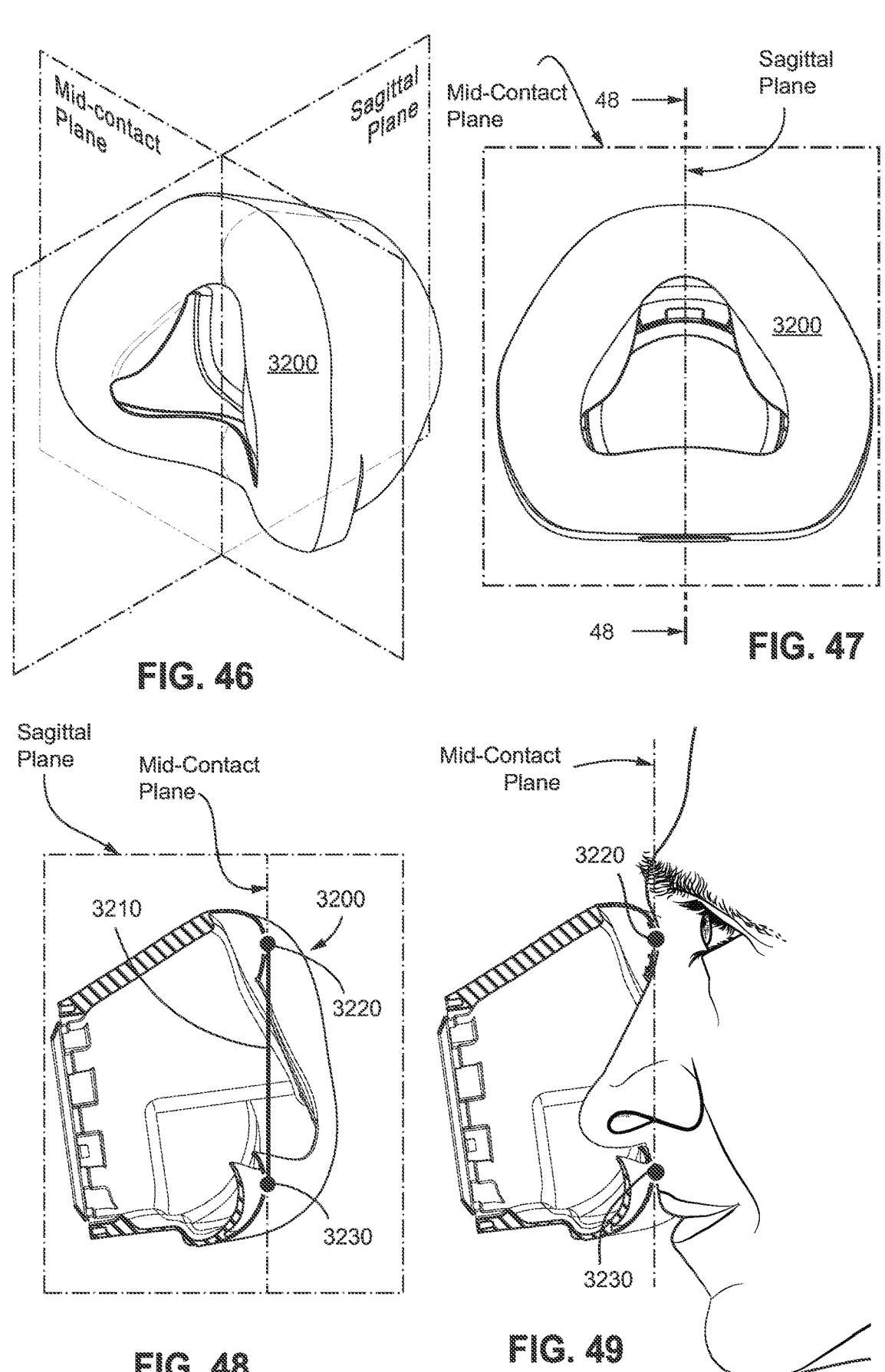

FIG. 46 shows a view of a patient interface 3000 showing a sagittal plane and a mid-contact plane.

FIG. 47 shows a view of a posterior of the plenum chamber of FIG. 46. The direction of the view is normal to the mid-contact plane. The sagittal plane in FIG. 47 bisects the patient interface 3000 into left-hand and right-hand sides.

FIG. 48 shows a cross-section through the patient interface of FIG. 47, the cross-section being taken at the sagittal plane shown in FIG. 47. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the patient interface at two points on the sagittal plane: a superior point 3220 and an inferior point 3230. Depending on the geometry of the cushion in this region, the mid-contact plane may be a tangent at both the superior and inferior points.

FIG. 49 shows the patient interface 3000 of FIG. 46 in position for use on a face. The sagittal plane of the patient interface 3000 generally coincides with the midsagittal plane of the face when the patient interface is in position for use. The mid-contact plane corresponds generally to the 'plane of the face' when the patient interface is in position for use. In FIG. 49 the patient interface 3000 is that of a nasal mask, and the superior point 3220 sits approximately on the sellion, while the inferior point 3230 sits on the lip superior.

3.4 RPT Device

Figure 50:
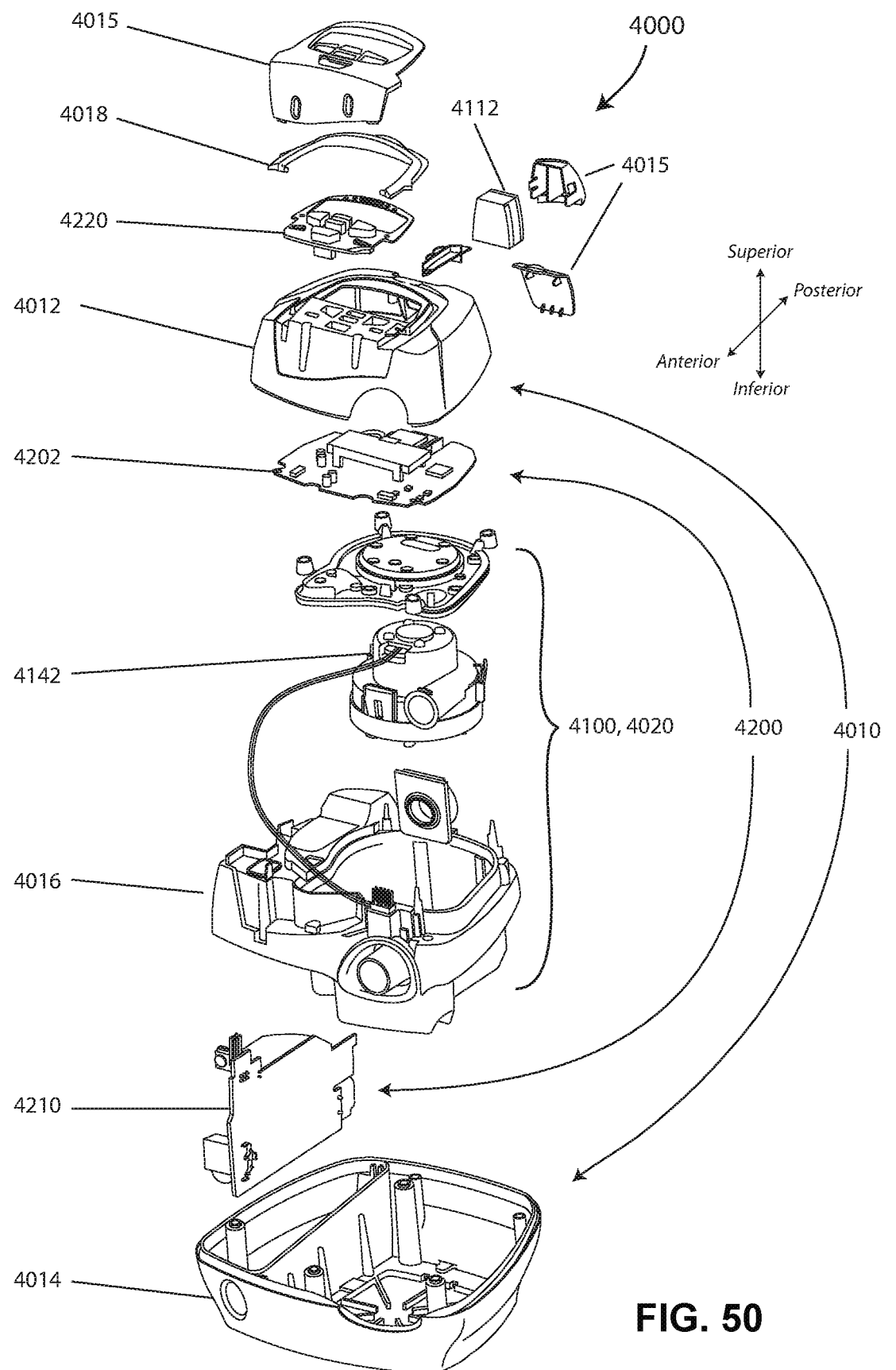

FIG. 50 shows an RPT device in accordance with one form of the present technology.

Figure 51:
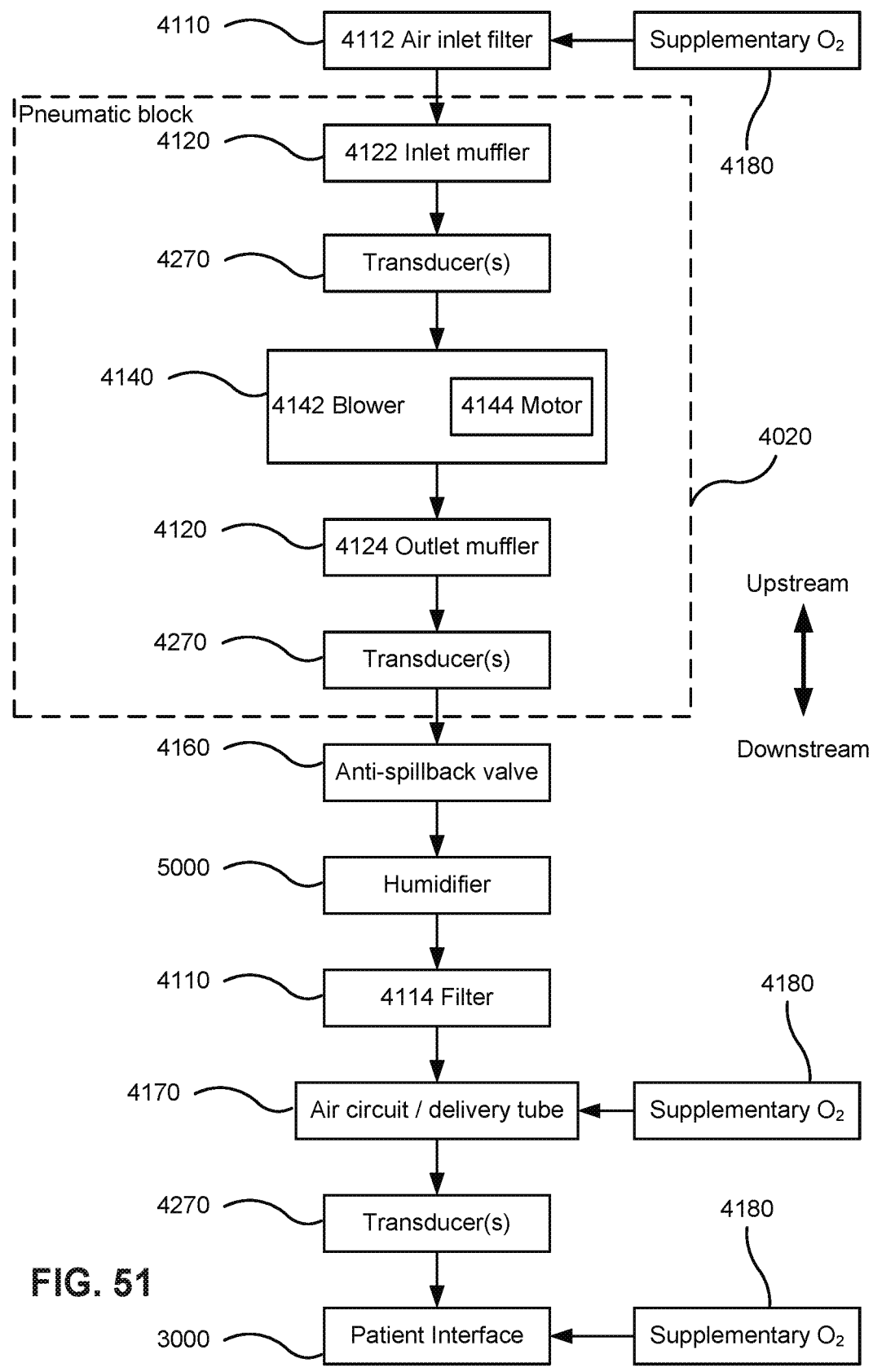

FIG. 51 is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 52:
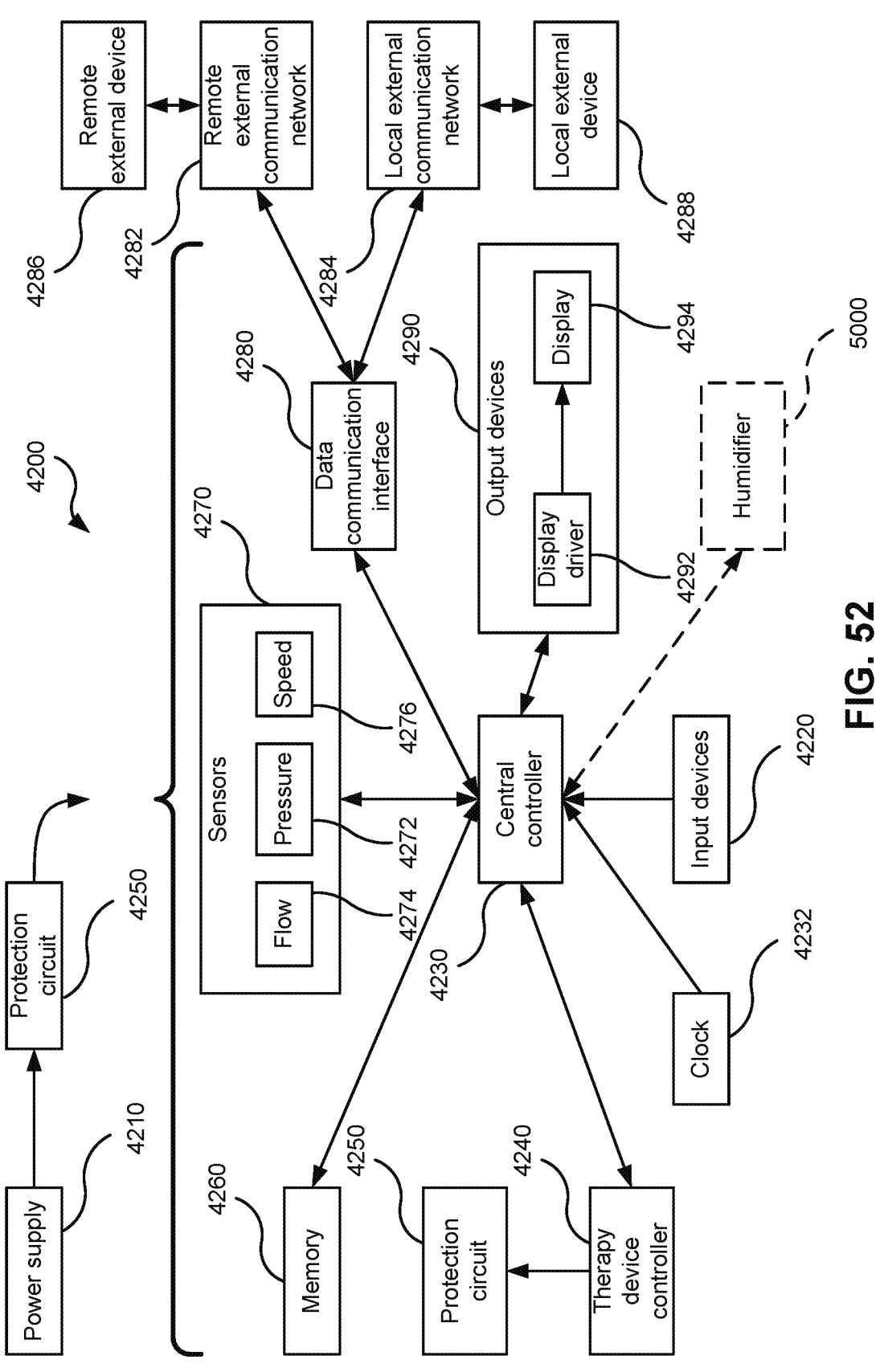

FIG. 52 is a schematic diagram of the electrical components of an RPT device in accordance with one form of the present technology.

Figure 53:
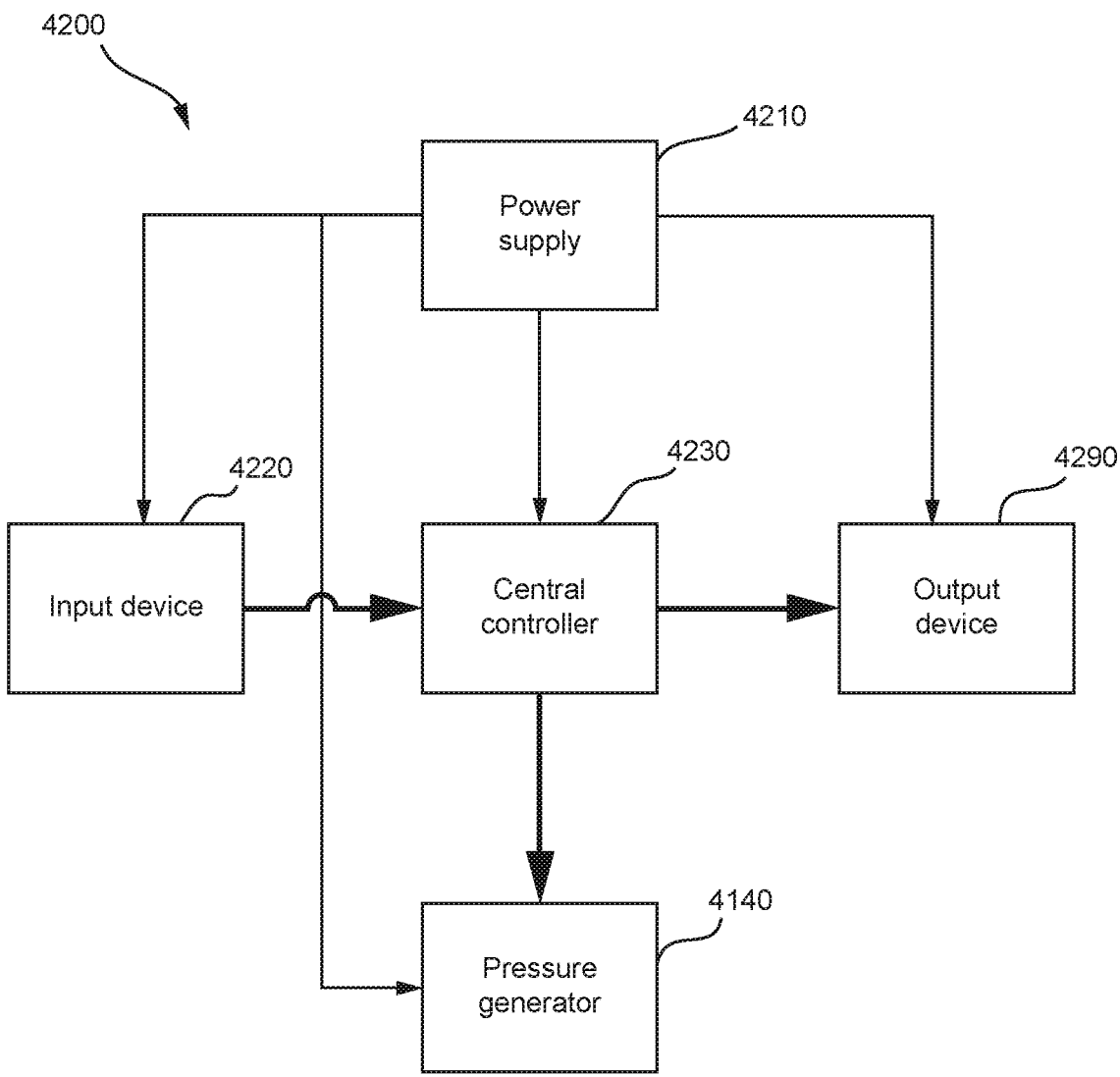

FIG. 53 is a schematic diagram of the algorithms implemented in an RPT device in accordance with one form of the present technology.

3.5 Humidifier

Figure 54:
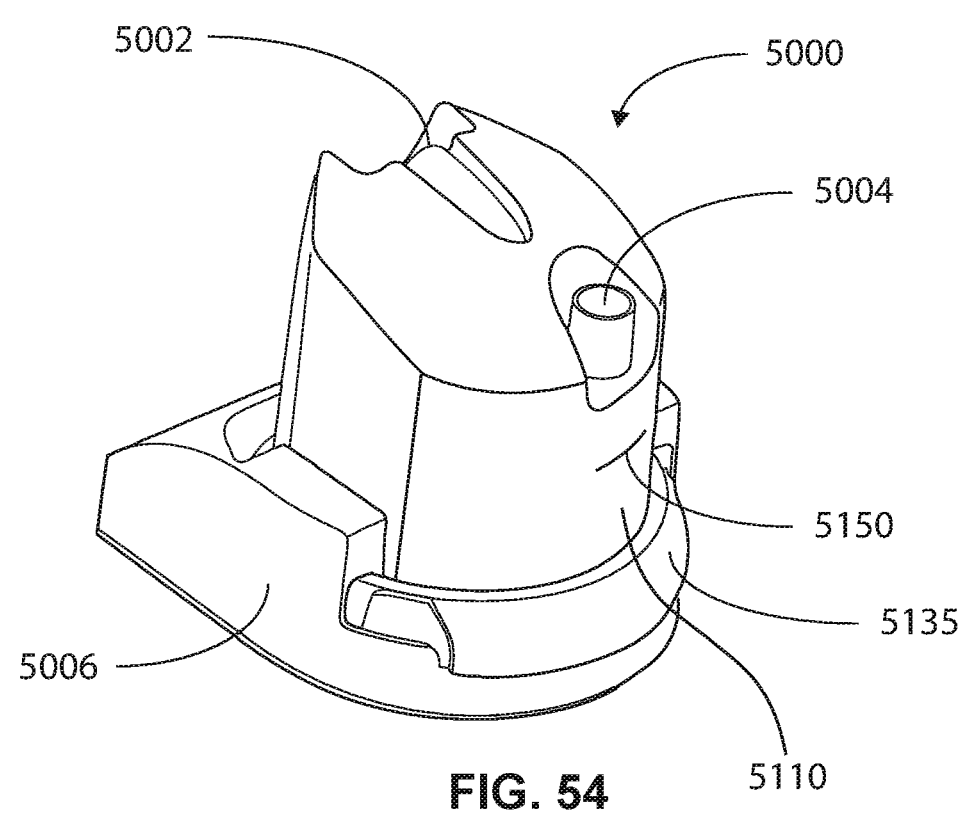

FIG. 54 shows an isometric view of a humidifier in accordance with one form of the present technology.

Figure 55:
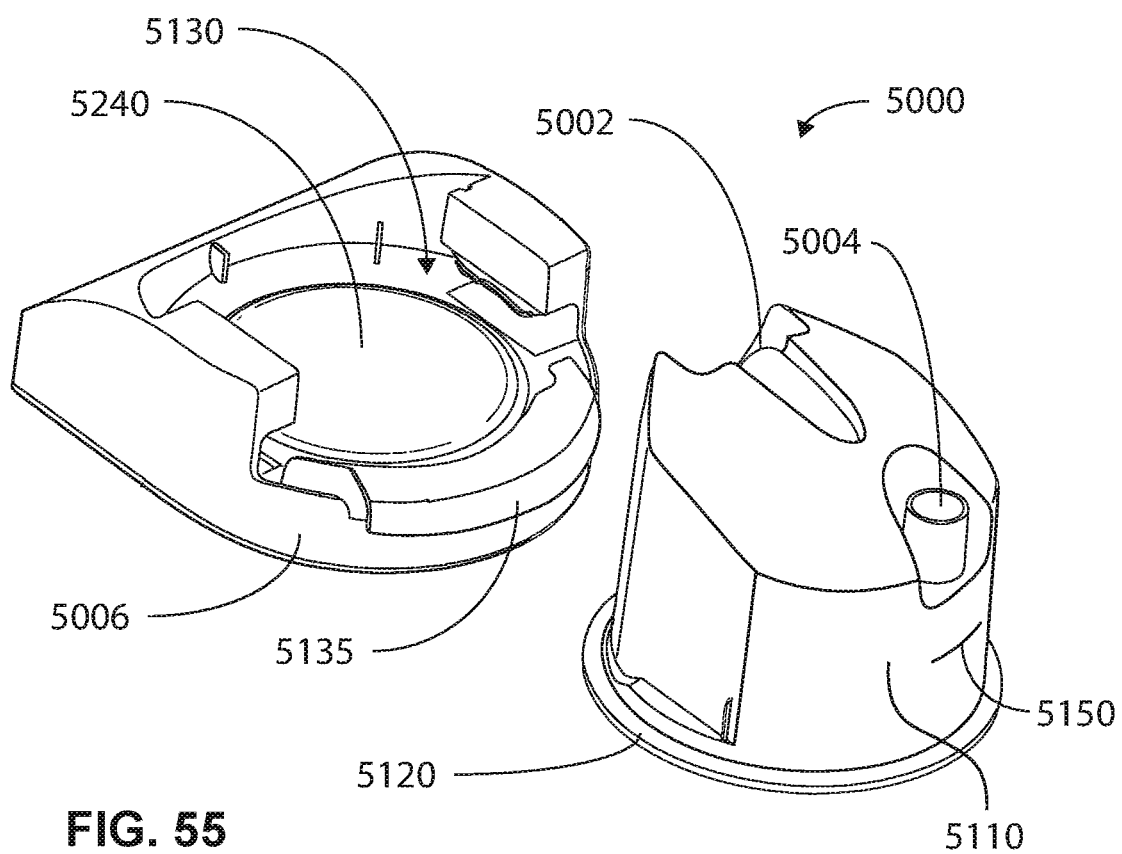

FIG. 55 shows an isometric view of a humidifier in accordance with one form of the present technology, showing a humidifier reservoir 5110 removed from the humidifier reservoir dock 5130.

Figure 56:
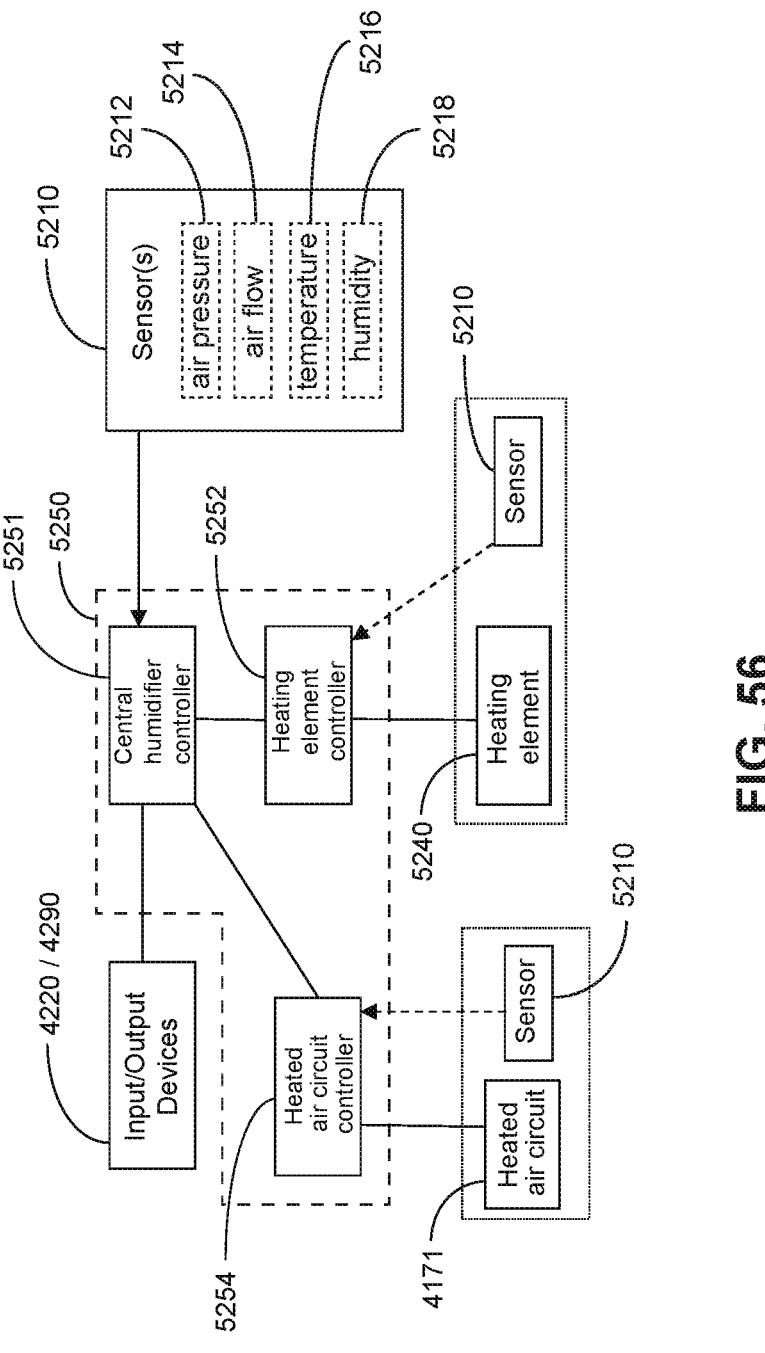

FIG. 56 shows a schematic of a humidifier in accordance with one form of the present technology.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 Respiratory Therapy Systems

In one form, the present technology comprises a respiratory therapy system for treating a respiratory disorder. The a respiratory therapy system may comprise an RPT device 4000 for supplying a flow of air to the patient 1000 via an air circuit 4170 and a patient interface 3000 or 3800.

4.3 Patient Interface

A non-invasive patient interface 3000 in accordance with one aspect of the present technology may comprise the following functional aspects: a seal-forming structure 3100, a shell or chassis 3200, a frame assembly 3300, a positioning and stabilising structure 3400, a vent 3500, and one form of connection port 3210 for connection to air circuit 4170. In some forms a functional aspect may be provided by one or more physical components. In some forms, one physical component may provide one or more functional aspects. In use the seal-forming structure 3100 may be arranged to surround an entrance to the airways of the patient so as to maintain positive pressure at the entrance(s) to the airways of the patient 1000. The sealed patient interface 3000 may therefore be suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology may be constructed and arranged to be able to provide a supply of air at a positive pressure of at least 6 cmH$_2$O with respect to ambient.

The patient interface 3000 in accordance with one form of the present technology may be constructed and arranged to be able to provide a supply of air at a positive pressure of at least 10 cmH$_2$O with respect to ambient.

The patient interface 3000 in accordance with one form of the present technology may be constructed and arranged to be able to provide a supply of air at a positive pressure of at least 20 cmH$_2$O with respect to ambient.

4.3.1 Seal-Forming Structure

In one form of the present technology, a seal-forming structure 3100 may provide a target seal-forming region, and may additionally provide a cushioning function. The target seal-forming region may be a region on the seal-forming structure 3100 where sealing occurs. The region where sealing actually occurs—the actual sealing surface—may change within a given treatment session, from day to day, and from patient to patient, depending on a range of factors including for example, where the patient interface was placed on the face, tension in the positioning and stabilising structure, and the shape of a patient's face.

In one form the target seal-forming region may be located on an outside surface of the seal-forming structure 3100.

In certain forms of the present technology, the seal-forming structure 3100 may be (at least in part) constructed from a biocompatible material, e.g. silicone rubber.

A seal-forming structure 3100 in accordance with the present technology may be constructed from a soft, flexible, resilient material such as silicone.

In certain forms of the present technology, a system may be provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

4.3.1.1 Sealing Mechanisms

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In certain forms of the present technology, a seal-forming structure may comprise one or more of a pressure-assisted sealing flange, a compression sealing portion, a gasket sealing portion, a tension portion, and a portion having a tacky or adhesive surface.

4.3.1.2 Nose Bridge or Nose Ridge Region

In one form, the non-invasive patient interface 3000 may comprise a seal-forming structure that forms a seal in use on a nose bridge region or on a nose-ridge region of the patient's face.

In one form, the seal-forming structure may include a saddle-shaped region constructed to form a seal in use on a nose bridge region or on a nose-ridge region of the patient's face.

4.3.1.3 Upper Lip Region

In one form, the non-invasive patient interface 3000 may comprise a seal-forming structure that forms a seal in use on an upper lip region (that is, the lip superior) of the patient's face.

In one form, the seal-forming structure may include a saddle-shaped region constructed to form a seal in use on an upper lip region of the patient's face.

4.3.1.4 Chin-Region

In one form the non-invasive patient interface 3000 may comprise a seal-forming structure that forms a seal in use on a chin-region of the patient's face.

In one form, the seal-forming structure may include a saddle-shaped region constructed to form a seal in use on a chin-region of the patient's face.

4.3.1.5 Foam Cushion and Undercushion

As shown in FIGS. 16-24B, the seal-forming structure 3100 may include a foam cushion 3105 mounted on an undercushion 3110, which in turn may be mounted on the shell or chassis 3200. The foam cushion 3105 may sealingly engage the patient's face when the seal-forming structure 3100 is mounted to the patient's face. The undercushion 3110 may provide support for the foam cushion 3105 and may assist forming the seal with the patient's face. The shell or chassis 3200 may provide rigid support to maintain the shape of the seal forming structure 3100. The shell or chassis 3200 may also provide an interface for retention of the frame assembly 3300.

The foam cushion 3105 may be a soft memory foam. For example, the foam cushion 3105 may be made of polyether and/or polyurethane material. In addition, the foam cushion 3105 may be configured to maintain a compression seal against the patient's skin.

FIG. 22 illustrates the foam cushion 3105 prior to being mounted and/or secured to the undercushion 3110. As can be seen, the foam cushion 3105 may be have a sealing surface 3115 that is configured to sealingly engage the patient's face. An attachment surface 3120 may oppose the sealing surface 3115 and may engage a corresponding surface of the under-cushion 3110. The sealing surface 3115 and the attachment surface 3120 may be substantially planar when the foam cushion 3105 is in the unmounted state. Manufacturing the foam cushion 3105 as a substantially planar component may make the manufacturing process simpler and easier. In addition, the thickness of the foam cushion 3105 may be substantially consistent throughout the foam cushion 3105 so that the distance between the sealing surface 3115 and the attachment surface 3120 may be substantially the same throughout the foam cushion 3105. The consistent thickness of the foam cushion 3105 may simplify the manufacturing process for the foam cushion 3105 and may make it easier and more cost effective to manufacture the foam cushion 3105. The consistent thickness may also make it easier to assemble the foam cushion 3105 to the undercushion 3110.

A hole 3125 may be formed through a central region of the foam cushion 3105 and may be bound by an inner surface 3126, thereby forming a gas flow path through the foam cushion 3105. At the same time, the perimeter of the foam cushion 3105 may be formed by a perimeter surface 3127. In addition, the sealing surface 3115 may meet the inner surface 3126 at a first rim 3130 at one end of the hole 3125, while the attachment surface 3120 may meet the inner surface 3126 at a second rim 3135 at the other end of the hole 3125. The widths of the sealing surface 3115 and the attachment surface 3120 (i.e., the distance between the rims of the hole 3125 and the perimeter surface 3127 of the foam cushion 3105) may be varied.

For example, as can be seen in FIG. 22, the widths w of the sealing surface 3115 and the attachment surface 3120 may be greater at a central superior region (or nose bridge region) 3140 of the foam cushion 3105 and at a central inferior region (or upper lip region) 3142 of the foam cushion 3105 than at other regions of the foam cushion 3105. The central superior region 3140 may be configured to engage the patient's nose bridge, while the central inferior region 3142 may be configured to engage the patient's upper lip region (lip superior) and/or the patient's columella.

The increased widths (widened regions 3145, 3150) may form indentations in the hole 3125 so that the hole 3125 is narrower at the central superior and central inferior regions 3140, 3142. In addition, the perimeter surface 3127 of the foam cushion 3105 may turn inward at the central inferior region 3142 to form a concave (or positive curvature) portion of the perimeter surface 3127. The inward turn of the perimeter surface 3127 may create an indentation in the foam cushion 3105 that may help improve comfort in the patient's upper lip region. The remaining portions of the perimeter surface 3127 may be convex (or have a negative curvature). At the same time, the inner surface 3126 at the central inferior and central superior regions 3140, 3142 may be convex (or may have a negative curvature) while the remaining portions of the inner surface 3126 may be concave (or may have a positive curvature).

As can be seen in FIG. 22, the shape of the hole 3125 may be different from the shape of the perimeter of the foam cushion 3105 due to the indentation in the perimeter at the central inferior location and due to the wider portions of the attachment and sealing surfaces 3115, 3120 at the central superior and central inferior regions 3140, 3142.

The shape of the foam cushion 3105 may conform to the micro differences and/or undulations in a user's face. In addition, when mounted to the undercushion 3110 (as shown in FIG. 21), the foam cushion 3105 may be folded or bent along a bisecting plane 3155 that bisects the foam cushion 3105 and extends through the central superior and central inferior regions 3140, 3142. When mounted to the undercushion 3110, the central superior region 3140 of the foam cushion 3105 may be in position to engage the patient's nose bridge. In addition, the central inferior region 3142 of the foam cushion 3105 may be in position to engage the patient's upper lip region (lip superior) and/or columella. Thus, the foam cushion 3105 may have an enlarged sealing area at the widened regions 3145, 3150 (i.e., at the patient's nose bridge and upper lip region (or lip superior)). The sealing area of the foam cushion 3105 (i.e., the portion of the foam cushion 3105 that comes into contact with the patient's face to form the seal against the patient's face) at the remaining areas may be less than at the widened regions 3145, 3150.

The increased sealing areas at the widened regions 3145, 3150 may provide extra surface area to engage the user's nose bridge and upper lip region (or lip superior). In addition, the extra surface area at the central superior region 3140 of the foam cushion 3105 (i.e., the portion configured to engage the patient's nose bridge) may improve the seal between the foam cushion 3105 and the patient's nose bridge and top sides of the patient's nose by providing enough surface area to maintain a seal with the patient's nose in dynamic situations (e.g., when the seal forming structure 3100 shifts relative to the user's nose). Also, the extra surface area at the central inferior region 3142 may form a ridge that may prevent the foam cushion 3105 from occluding the patient's nostrils when the seal forming structure 3100 shifts relative to the patient's nose (e.g., mask ride-up). In particular, the ridge may engage the patient's columella before the rest of the inferior portion of the foam cushion 3105 can reach the patient's nostril openings, thereby preventing the rest of the inferior portion of the foam cushion 3105 from reaching and occluding the patient's nostril openings. Without the ridge, there would be nothing to block the inferior portion of the foam cushion 3105 from reaching the patient's nostril openings when the patient interface rides up.

When mounted on the undercushion 3110, the shape of the foam cushion 3105 may be transformed so that the sealing surface 3115 at the central inferior region 3142 (which may be configured to sealingly engage the patient's columella and/or lip superior) may have a positive curvature across by the bisecting plane 3155. It is contemplated that the central inferior region 3142 may also be a saddle region. The central inferior region 3142 may be flanked by a pair of lower corner regions 3156 configured to engage the lower corners of the patient's nose. The sealing surface 3115 at the pair of lower corner regions 3156 may have a negative curvature. In addition, it is contemplated that each of the pair of lower corner regions 3156 may be dome shaped.

The sealing surface 3115 at the central superior region 3140 (which may be configured to sealingly engage the patient's nose bridge) may be folded along the bisecting plane 3155. Alternatively, the sealing surface 3115 at the central superior region 3140 may have a positive curvature across the bisecting plane 3155. It is contemplated that the central superior region 3140 may be saddle shaped. It is further contemplated that the positive curvature at the central superior region 3140 may be greater than the positive curvature at the central inferior region 3142. In addition, the central superior region 3140 may be flanked by a pair of top side regions 3157 configured to engage the top sides of the patient's nose. The sealing surface 3115 at the top side regions 3157 may have a negative curvature. In addition, it is contemplated that each of the pair of top side regions 3157 may be dome shaped.

The left hand top side region 3157 and the left hand lower corner region 3156 may be separated from each other by an intermediate region 3158 with a positive curvature. Similarly, the right hand top side region 3157 and the right hand lower corner region 3156 may be separated from each other by an intermediate region 3159 with a positive curvature. The positive curvature of both intermediate regions 3158, 3159 may be across a lateral axis 3161 that extends from the intermediate region 3158 to the intermediate region 3159. In addition, both the intermediate region 3158 and the intermediate region 3159 may be saddle shaped.

As discussed above, the sealing surface 3115 of the foam cushion 3105 may have four dome shaped regions, four saddle shaped regions (or three saddle shaped regions when the central superior region 3140 is not saddle shaped), and eight transition regions between the dome and saddle regions in which the shape of the sealing surface 3115 transitions from saddle to dome and vice versa.

The undercushion 3110 may be made of a translucent silicone rubber with a single wall construction. The elastomeric wall thickness of the undercushion wall may vary in different sections to ensure accommodation of a wide fit range and to ensure that spring forces generated from the undercushion 3110 are tuned to maximize compression of the foam cushion 3105. The undercushion 3110 itself may not create a seal with the patient's face (the seal may be created between the foam cushion 3105 and the patient's face). Instead, the undercushion 3110 may provide additional compliance and may allow the seal forming structure

3100 to move dynamically along the patient's face with minimal compression loss to the foam cushion 3105. In sensitive regions of the patient's face (particularly the patient's nose bridge region and/or the patient's upper lip region), the undercushion 3110 may be deliberately thinned to optimize comfort.

The undercushion 3110 may comprise a support wall 3160 extending from the chassis 3200 to the foam cushion 3105 and providing structural support to the foam cushion 3105. The support wall 3160 may terminate at a support flange 3165. The support flange 3165 may be cantilevered from the support wall 3160. In addition, the support flange 3165 may extend from the support wall 3160 radially inwardly toward a center of the airflow path within the patient interface 3000. The support flange 3165 may have an outer surface 3162 to which the attachment surface 3120 of the foam seal 3105 may be secured. The attachment surface 3120 may be secured to the support flange 3165 by way of bonding or adhesive. The adhesive may be a liquid silicone rubber.

The support wall 3160 may include a superior gusset 3170 at a superior region of the support wall 3160 corresponding to the patient's nasal bridge. The superior gusset 3170 may straddle the bisecting plane 3155. In addition, the thickness of the support wall 3160 at the central superior region (or the apex or the nose bridge region) 3140 may be thinner than at other regions of the support wall 3160. In addition, the thickness of the support wall 3160 in the central superior region (or the apex or the nose bridge region) 3140 may decrease from the superior gusset 3170 to the support flange 3165. For example, the thickness of the support wall 3160 at the superior gusset 3170 (or at least the indentation portion of the gusset 3170) may be 0.70 to 0.75 mm (e.g., 0.72 mm), while the thickness of the portion of the support wall 3160 between the superior gusset 3170 and the support flange 3165 may be 0.40 to 0.45 mm (e.g., 0.42 mm).

The superior gusset 3170 and the thinner elastomeric wall may allow the nasal bridge portion of the seal forming structure 3100 to be more compliant without increasing the compression of the foam cushion 3105. The increased compliance may improve comfort and reduce pressure across the patient's nose bridge and may reduce red marks on the patient's face.

The support wall 3160 may include a pair of thickened regions 3175 flanking the superior gusset 3170. The thickened regions 3175 may provide stable support for an adequate seal at the patient's alar facial junction. The thickened regions 3175 may be the thickest portions of the support wall 3160. For example, the thickened regions 3175 may be 1.80 to 1.90 mm (e.g., 1.85 mm) thick. The thickened regions 3175 may not extend all of the way to the support flange 3165. Alternatively, thickened regions 3175 may extend all of the way to the support flange 3165. The thickened regions 3175 may increase the stability of the seal at a location that is most susceptible to leak and discomfort.

An inferior gusset 3180 may be located opposite the superior gusset 3170 at the central inferior region 3142 of the seal forming structure 3100. The inferior gusset 3180 may straddle the bisecting plane 3155. The elastomeric wall thickness of the support wall 3160 at the inferior gusset 3180 and at the central inferior region (the soft upper lip region) 3142 may be less than the elastomeric wall thickness at the rest of the support wall 3160 except for the part of the support wall 3160 at the superior gusset 3170 and at the central superior region 3140. For example, the elastomeric wall thickness of the support wall 3160 at the central inferior portion 3142 and the inferior gusset 3180 may range from 0.55 mm to 0.85 mm. It is contemplated that a most inferior portion of the support wall 3160 (e.g., a central portion of the inferior gusset 3180) may be 0.55 mm thick, while portions of the support wall 3160 flanking the most inferior portion (e.g., the lateral portions of the inferior gusset 3180) may be 0.85 mm thick.

The rest of the support wall 3160 may be 1.50 to 1.70 mm (e.g., 1.60 mm). The superior gusset 3170 and the inferior gusset 3180 may be arranged so that collapsing the inferior gusset 3180 may pivot the seal forming structure 3100 around an axis 3185 that extends through the seal forming structure 3100 between the superior gusset 3170 and the inferior gusset 3180. It is contemplated that in some configurations, the axis 3185 and the lateral axis 3161 may be the same axis. In other configurations, they may be parallel to each other. It is further contemplated that the thickened regions 3175 may form a pivot point on the support wall 3160 around which the seal forming structure 3100 may pivot. Alternatively, the pivot point on the support wall 3160 may be between the thickened regions 3175 and the inferior gusset 3180 (i.e., outside of the thickened regions 3175).

It is contemplated that a depth of the one or more indentations of the inferior gusset 3185 may be consistent or may be varied. For example, the depth of the one or more indentations may increase toward lateral sides of the inferior gusset 3185 so that the one or more indentations at a central region of the inferior gusset 3185 may be shallower than at lateral regions. Alternatively, the one or more indentations may be deepest at the central region and may become shallower toward the lateral regions.

In addition, in cases with multiple indentations, the depths of the indentations may be different. For example, the depth of one or more indentations may be consistent, while the thickness of one or more indentations may be varied as discussed in the previous paragraph. It should also be understood that the depth of the one or more indentations of the superior gusset 3170 may be varied or consistent as discussed above.

The support flange 3165 may have a surface (i.e., the outer surface 3162) to which the foam cushion 3105 may be attached. It is contemplated that an angle α between the support wall 3160 and the support flange 3165 may be 90 degrees or less. In addition, the support flange 3165 may extend from a perimeter of the seal forming structure 3100 toward the interior of the seal forming structure 3100 (i.e., inwardly from the perimeter). In addition, the support flange 3165 may be flexible in a manner that allows the angle α between the support flange 3165 and the support wall 3160 to be variable depending on the amount of force acting on the foam cushion 3105 (and by extension the amount of force acting on the support flange 3165). When in the neutral state (i.e., no forces acting on the seal-forming structure 3100), the angle α may vary in different regions of the support flange 3165. The different angles α may allow the foam cushion 3105 to follow the contours of the patient's face.

The support flange 3165 may be made of the same material as the support wall 3160. In addition, the support flange 3165 may be unitarily formed with the support wall 3160. It is contemplated that the support flange 3165 may simply be an extension of the support wall 3160 that is bent radially inwardly toward the interior of the seal forming structure 3100. Alternatively, the support flange 3165 may be formed separately from and assembled to the support wall 3160. In this configuration, the support flange 3165 may be secured to the support wall 3160 by mechanical fastener, adhesive, or bonding.

Due to the flexibility of the support flange 3165, the support flange 3165 may flex due to the pressure of the respiratory gas inside the patient interface 3000. When such flexing of the support flange 3165 causes angle α between the support flange 3165 and the support wall 3160 to exceed a predetermined threshold an undesirable condition called "blow out" occurs. An occurrence of "blow out" may compromise the sealing ability of the foam cushion 3105. The threshold may be greater than 90 degrees. In some cases, the threshold may be less than 90 degrees. It is contemplated that the threshold angle may be any angle that may compromise the seal-forming capability of the foam cushion 3105. Alternatively, the threshold angle may be the angle α that exists between the support flange 3165 and the support wall 3160 when the seal-forming structure 3100 is in a neutral state (i.e., no force acting on the support flange 3165).

To prevent "blow out", the seal-forming structure 3100 may include preventive components. For example, the seal-forming structure 3100 may include one or more ribs 3190 connected to the support flange 3165 and the support wall 3160. The ribs 3190 may prevent the portions of the support flange 3165 attached to the ribs from flexing outwardly and increasing the angle α. The ribs 3190 may also reduce the amount of outward flexing of the support flange 3165 in areas adjacent the ribs 3190. It is contemplated that the ribs 3190 may be flexible and/or compressible, thereby allowing the support flange 3165 to move relative to the support wall 3160 when the foam cushion 3105 is subjected to a compressive force. For example, the ribs 3190 may allow the support flange 3165 to move to decrease the angle α between the support wall 3160 and the support flange 3165.

As shown in FIG. 20, a pair of ribs 3190 may be positioned adjacent the inferior gusset 3180 (the second rib 3190 of the pair is hidden by the foam cushion 3105). It is contemplated that each rib 3190 may be 0.60 to 0.80 mm (e.g., 0.70 mm) thick. In addition, the ribs 3190 may flank the bisecting plane 3155 in the inferior region of the foam cushion 3105.

As can be seen in FIGS. 20 and 23, the support flange 3165 may extend a certain distance from the support wall 3160. The distance by which the support flange 3165 extends from the support wall 3160 is the width of the support flange 3165. The width of the support flange 3165 may provide a platform or surface to which the attachment surface 3120 of the foam cushion 3105 may be attached. As can be seen in FIG. 23, the width of the support flange 3165 may be less than the width of the attachment surface 3120 of the foam cushion 3105. Thus, a portion of attachment surface 3120 may overhang the support flange 3165. Allowing the foam cushion 3105 to overhang the support flange 3165 may promote rolling in of the foam cushion 3105, which resists "blow out". However, too much inward rolling may cause discomfort due to contact with the undercushion 3110 and more load on the patient's face. Accordingly, there may be relatively less overhang in areas prone to discomfort such as the nose bridge region and the upper lip region (or lip superior).

Another component configured to prevent "blow out" of the seal-forming structure 3100 may be an extended region (or flap portion) 3195 of the support flange 3165. The extended region 3195 may be located at the central superior region of the seal-forming structure 3100 (i.e., the portion of the seal-forming structure 3100 configured to engage the patient's nose bridge) and may be a region of the support flange 3165 in which the width of the support flange 3165 is greatest. The extended region 3195 may take the form of a flap that extends beyond the width of the adjacent portions of the support flange 3165.

In addition, the extended region 3195 may straddle the bisecting plane 3155 that bisects the seal-forming structure 3100 through the central superior and inferior regions 3140, 3142 of the seal-forming structure 3100. The extended region 3195 may have a positive curvature (i.e., a concave shape) across the bisecting plane 3155. In addition, it is contemplated that the outer surface 3162 of the extended region 3195 may have a saddle shape. The increased width and the curved surface of the extended region 3195 may help resist "blow out" by resisting an inversion of the curvature of the extended region 3195 (i.e., the positive curvature of the outer surface 3162 changing to a negative curvature) due to pressure in the plenum chamber. Thus, the extended region 3195 may eliminate the need for ribs in the superior region of the seal-forming structure 3100. As can be seen in FIG. 23, due to the increased width of the extended region 3195, the overhang of the central superior region 3140 of the foam cushion 3105 may be less than the overhang of the central inferior region 3142 of the foam cushion 3105. Alternatively, due to the increased width of the widened region 3145, the overhang of the foam cushion 3105 over the support flange 3165 may be consistent throughout the seal-forming structure 3100.

The extended region 3195 of the support flange 3165 may correspond to the central superior region 3140 of the foam cushion 3105. In addition, the top side regions 3157 may overlap the lateral sides of the extended region 3195 of the support flange 3165. Alternatively, the top side regions 3157 may be adjacent the extended region 3195 of the support flange 3165.

It is contemplated that the elastomeric wall thickness of the support flange 3165 may vary in different regions. For example, the elastomeric wall thickness of the support flange 3165 may be thinner in the central superior region 3140 and in the central inferior region 3142 than in other regions of the support flange 3165. The thinner elastomeric wall of the support flange 3165 may allow for more compliance of the foam cushion in regions that are more sensitive to pressure. In addition, the inclusion of ribs 3190 in the inferior region of the seal-forming structure 3100 and the inclusion of the extended region 3195 in the central superior region 3140 may allow the support flange 3165 to be thinner in those regions without compromising the resistance to "blow out".

It is further contemplated that the elastomeric wall thickness of the support flange 3165 may increase toward the support wall 3160. For example, an end of the support flange 3165 furthest from the support wall 3160 (i.e., the cantilevered end) may be thinner than an end of the support flange 3165 that is attached to the support wall 3160. It the elastomeric wall thickness of the support flange 3165 may vary in abrupt "steps" or may gradually taper. In addition, the support flange 3165 may be tapered or "stepped" in certain regions of the support flange 3165 (the central inferior region 3145) and may have a consistent elastomeric wall thickness in other regions (e.g., intermediate regions). Alternatively, the elastomeric wall thickness of all of the regions of the support flange may be consistent. Making the support flange 3165 thicker where it is connected to the support wall 3160 may reinforce the support flange 3165 or make the support flange 3165 more resistant to flexing or "blow out".

The curvature of the outer surface 3162 of the support flange 3165 may correspond to the curvature of the sealing surface 3115 of the foam cushion 3105. For example, as discussed above, the outer surface 3162 at the extended region 3195 may have a positive curvature (concave shape) that straddles the bisecting plane 3155 (similar to the curvature of the sealing surface 3115 at the central superior region 3140). In addition, it is contemplated that the extended region 3195 may be saddle shaped.

The outer surface 3162 at the central inferior region 3142 may have a positive curvature (concave shape) that straddles the bisecting plane 3155 (similar to the curvature of the sealing surface 3115 at the central inferior region 3142). In addition, it is contemplated that the central inferior region 3142 of the support flange 3165 may be saddle shaped.

The central inferior region 3142 of the support flange 3165 may be flanked by a pair of lower corner regions 3196 in locations that correspond to the lower corner regions 3156 of the foam cushion 3105. The outer surface 3162 at the lower corner regions 3196 may have a negative curvature (convex shape). In addition, it is contemplated that the lower corner regions 3196 may be dome shaped.

It is further contemplated that the positive curvature of the outer surface 3162 at the extended region 3195 may be greater than the positive curvature of the outer surface 3162 at the central inferior region 3142. In addition, the extended region 3195 may be flanked by a pair of top side regions 3197 in locations that correspond to the top side regions 3157 of the foam cushion 3105. The outer surface 3162 at the top side regions 3197 may have a negative curvature (convex shape). In addition, it is contemplated that the top side regions 3197 may be dome shaped.

The left hand top side region 3197 and the left hand lower corner region 3196 may be separated from each other by an intermediate region 3198 with a positive curvature. Similarly, the right hand top side region 3197 and the right hand lower corner region 3196 may be separated from each other by an intermediate region 3199 with a positive curvature. The positive curvature of both intermediate regions 3198, 3199 may be across the lateral axis 3161. In addition, both the intermediate region 3198 and the intermediate region 3199 may be saddle shaped.

As discussed above, the outer surface 3162 of the support flange 3165 may have four dome shaped regions, four saddle shaped regions, and eight transition regions between the dome and saddle regions in which the shape of the outer surface 3162 transitions from saddle to dome and vice versa.

4.3.2 Shell or Chassis

The shell or chassis 3200 has a perimeter that is shaped to be complementary to the surface contour of the face of an average person in the region where a seal will form in use. Actual contact with the face may be provided by the seal-forming structure 3100. The seal-forming structure 3100 may extend in use about the entire perimeter of the shell or chassis 3200.

The shell or chassis 3200 may be permanently (e.g., co-molded, overmolded) or removably (e.g., mechanical interlock) connected to the undercushion 3110. It is contemplated that the undercushion 3110 may be constructed of a relatively flexible or pliable material (e.g., silicone) and the shell or chassis 3200 may be constructed of a relatively rigid material (e.g., polycarbonate). The shell or chassis 3200 and the undercushion 3110 may cooperate to form a plenum chamber 3205. Alternatively, the shell or chassis 3200 and the undercushion 3110 may be formed from a single homogeneous piece of material.

The shell or chassis 3200 may not cover the eyes of the patient in use. In other words, the eyes may be outside the pressurised volume defined by the shell or Chassis 3200.

Such forms tend to be less obtrusive and/or more comfortable for the wearer, which can improve compliance with therapy.

The shell or chassis 3200 may be constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

Alternatively, the shell or chassis 3200 may be constructed from a translucent material. The use of a translucent material can reduce the obtrusiveness of the patient interface, and help improve compliance with therapy.

The shell or chassis 3200 may include an opening 3211 by which breathable gas may be delivered to the plenum chamber 3205. The opening 3211 may be bounded by an annular flange 3215 which may be adapted to be connected to the frame assembly 3300 and adapted to interface (e.g., seal) with the air circuit 4170.

The shell or chassis 3200 may include a flexible sealing membrane or lip seal 3225 to provide a seal with the air circuit 4170. The lip seal 3225 may be attached to a rim of the opening 3211 and may include a free end that extends radially inwardly into the opening 3211. An end of the air circuit 4170 may be structured and arranged to sealingly engage with the lip seal 3225 to form a seal for the air flow path. It is contemplated that the sealing mechanism between the air circuit 4170 and the shell or chassis 3200 may be separate from the retention features that couple the air circuit 4170 to the shell or chassis 3200 or the frame assembly 3300.

The shell or chassis 3200 may form the plenum chamber 3205 for delivery of pressurised gases to the entrance of a patient's airways. The shell or chassis may be a rigid structure that directs a force onto the seal-forming structure 3100 for sealing to a patients face. The force may be provided by tension forces from tightening the headgear straps of the positioning and stabilising structure 3400. These forces may be translated from a pair of upper and lower headgear straps to corresponding upper and lower arms of the frame assembly 3300.

The opening 3211 in the shell or chassis 3200 may be oriented relative to the foam cushion 3105 so that the opening 3211 faces downward when worn by user. As shown in FIGS. 24 and 24B, a central longitudinal axis 3212 of the opening 3211 may be oriented so that a portion of the central longitudinal axis 3212 outside of the patient interface 3000 extends in an inferior direction. As can be seen, the central longitudinal axis 3212 may form an angle β with the user's Frankfort horizontal plane 3213. It is contemplated that the angle β may be 10 to 50 degrees (e.g., 20 to 30 degrees). By orienting the opening 3211 in the downward direction, the opening 3211 may be better oriented relative to the patient's nostrils to improve washout of $CO_2$.

As discussed above, the support wall 3160 may include the inferior gusset 3180. The inferior gusset 3180 may be configured to be more compliant than the superior gusset 3170 (i.e., more easily collapsed than the superior gusset 3170) so that the support wall 3160 bends around the lateral axis 3185. Such a bending of the support wall 3160 may cause the orientation of the opening 3211 to shift so that the angle β increases when the inferior gusset 3180 is compressed. In addition, the portion of the central longitudinal axis 3212 of the opening 3211 outside the patient interface 3000 may rotate toward the inferior direction.

The bending of the support wall 3160 due to the collapse of the inferior gusset 3180 may occur when the patient interface 3000 is secured to the patient's face by the positioning and stabilzing structure 3400. In particular, tension forces from the positioning and stabilizing structure 3400 may cause the seal-forming structure 3100 to press against the contours of the patient's face. When pressed against the contours of the patient's face, the inferior gusset 3180 may be subject to a compressive force and may at least partially collapse, thereby causing the seal-forming structure 3100 to shift (or pivot) from a neutral position (i.e., a position in which the inferior gusset 3180 is not subject to a compressive force). The pivoting of the seal-forming structure 3100 may cause the portion of the central longitudinal axis 3212 outside of the patient interface 3000 may rotate toward the inferior direction and increase the angle $\beta$ with respect to the patient's Frankfort horizontal plane.

4.3.3 Frame Assembly

The frame assembly 3300 may include a shroud (or anchor wall) 3305 and a headgear connector 3310 attached to the shroud 3305 to provide a 4-point connection to the positioning and stabilizing structure 3400. The shroud 3305 (e.g., constructed of a relatively hard plastic material such as polycarbonate) may include an opening 3315 with an annular edge structured to engage with the air circuit 4170. The posterior or rear side of the shroud 3305 may include a plurality of locking tabs or spring arms 3320 (e.g., 2, 3, 4, 5, or more tabs or spring arms) spaced around the opening 3315 and structured to provide a mechanical interlock, e.g., snapfit connection, with the shell or chassis 3200.

The headgear connector 3310 may include a shroud connection portion 3325 connected to the shroud 3305, a pair (i.e., right and left) of upper headgear connector arms 3330 structured to connect to respective upper headgear straps of the stabilising structure 3400, a pair (i.e., right and left) of lower headgear connector arms 3335 structured to connect to respective lower headgear straps of the stabilizing structure 3400, and intermediate portions 3340 to interconnect the upper and lower arms 3330, 3335 with the shroud connection portion 3325.

Each upper headgear connector arm 3330 may include an upper headgear connection point in the form of a slot 3345 structured to receive a respective upper headgear strap of the stabilising structure 3400. Each lower headgear connector arm 3335 may include a lower headgear connection point in the form of a magnetic connector 3350 structured to locate and connect to a magnet associated with a respective lower headgear strap of the stabilising structure 3400. However, it should be appreciated that the upper and lower headgear connector arms 3330, 3335 may be connected with headgear straps of the headgear in other suitable manners.

The upper and lower headgear connector arms 3330, 3335 may be rigidised or stiffened such that that they may maintain a preformed 3D shape (not floppy) structured to conform to the facial profile and positions the upper headgear connection points in the appropriate locations. Each upper and lower headgear connector arms 3330, 3335 may maintain its preformed shape due to its rigidity or stiffness in particular orientations. The upper and lower headgear connector arms 3330, 3335 may be structured to be less resistant (less stiff or rigid) to bending into and away from the face to adapt varying facial widths. The upper and lower headgear connector arms 3330, 3335 may be rigidised such that they do not substantially deform under tension forces applied by the headgear straps, thereby acting as an intermediary between the headgear straps and the chassis 3200 to convert the tension forces from the headgear straps to a compressive force applied on the seal-forming structure 3100 to provide seal and stability on the face. The upper and lower headgear connector arms 3330, 3335 may also be shaped to apply the appropriate force vectors on the seal-forming structure 3100 via the shell or chassis 3200 to effect a stable and comfortable seal. In an example, the seal-forming structure 3100 may be pulled into the patient's face under the appropriate compressive force that may also be in line with the Frankfort horizontal plane 3213 (that is pulled directly back into the face.

The upper and lower headgear connector arms 3330, 3335 may also be rigidised to provide torsional rigidity to be resistant to deformation under twisting. The upper and lower headgear connector arms 3330, 3335 may also be resistant to bending deformation vertically up and down alongside the face (e.g., remain at the correct height relative to the ears). However, the upper and lower headgear connector arms 3330, 3335 may also be structured to provide a predetermined level of deformation to allow bending (allows bending towards/away from the face) to adjust for varying facial width. In addition, the upper and lower headgear connector arms 3330, 3335 may be resilient/elastic in this orientation to allow the upper and lower headgear connector arms 3330, 3335 to return to their original positions. This feature may also prevent discomfort by minimising the load/force exerted by the frame assembly on the face when the headgear straps are tightened by absorbing some of these tension forces due to its flexibility. In some locations, the upper and lower headgear connector arms 3330, 3335 may also provide rigidity/stiffness to avoid contact of the face, wherein the upper and lower headgear connector arms 3330, 3335 may act as a strut to resist bending deformation or compression into the face from headgear tension. Conversely, in other locations, the flexibility of the upper and lower headgear connector arms 3330, 3335 may allow the upper and lower headgear connector arms 3330, 3335 to collapse under tension or compression from side load (e.g., when a patient sleeps on their side), thereby exerting a side load on the patient interface. The upper and lower headgear connector arms 3330, 3335 may absorb the compressive force applied by the side load and prevent it from dislodging the seal-forming structure 3100. This flexibility may also allow for better conformation to the patient's face, which may increase comfort and may also prevent seal instability from side load.

It is contemplated that the lower headgear connector arms 3335 may optionally be relatively more flexible than the upper headgear connector arms 3330, e.g., the lower headgear connector arms 3335 may have less resistance against torsion such that they may twist with the lower headgear straps of the stabilising structure 3400. This flexibility may allow the lower headgear connector arms 3335 to twist and turn with the lower headgear straps to prevent forced disconnection of the retention features under these forces, i.e., maintain connection of the lower headgear connector arms 3335 with the lower headgear straps.

Each intermediate portion 3340 of the headgear connector 3310 assembly may include a flexible portion 3355 to conform to varying facial profiles, e.g., accommodate facial width variations. It is contemplated that the flexible portion 3355 comprises an indentation (on anterior and/or posterior sides) forming a hinging section adjacent the shell or chassis 3200.

The headgear connector 3310 may include a multi-layered configuration, e.g., layers of different materials to provided desired flexibility. It is contemplated that the headgear connector may be more rigid than the headgear straps of the stabilising structure 3400.

An inner (or posterior) surface of the shroud 3305 may engage an outer surface of the shell or chassis 3200. The shell or chassis 3200 may also comprise separate retention features or may be otherwise structured to detachably couple to the inner surface of the frame assembly 3300. The patient interface 3000 may be modular in that a single frame assembly size may be capable of connection to shroud or chassis sizes (e.g., small to large). Thus, the shell or chassis 3200 may also detachably couple to the frame assembly 3300 such that the frame assembly 3300 may be connected into a predetermined configuration that corresponds to its respective shell or chassis size. For example, smaller shells or chassis 3200 may have an overall reduced height relative to medium or large cushion assemblies. Thus the frame assembly 3300 may connect in a position relative to the cushion assembly to position the upper headgear attachment points 3345 in their correct position (between the eyes and ears, while providing an attachment point where the upper headgear straps avoid the ears). This means that the frame assembly 3300 may connect at a higher position on the shell or chassis 3200 when compared to medium or large shell or chassis sizes. In an example, medium and/or large sizes may not have this requirement and may connect such that the frame assembly 3300 may be positioned in substantially the same position.

4.3.4 Positioning and Stabilising Structure

The seal-forming structure 3100 of the patient interface 3000 of the present technology may be held in sealing position in use by the positioning and stabilising structure 3400.

In one form the positioning and stabilising structure 3400 may provide a retention force at least sufficient to overcome the effect of the positive pressure in the plenum chamber to lift off the face.

In one form the positioning and stabilising structure 3400 may provide a retention force to overcome the effect of the gravitational force on the patient interface 3000.

In one form the positioning and stabilising structure 3400 may provide a retention force as a safety margin to overcome the potential effect of disrupting forces on the patient interface 3000, such as from tube drag, or accidental interference with the patient interface.

In one form of the present technology, a positioning and stabilising structure 3400 may be provided that is configured in a manner consistent with being worn by a patient while sleeping. In one example the positioning and stabilising structure 3400 may have a low profile, or cross-sectional thickness, to reduce the perceived or actual bulk of the apparatus. In one example, the positioning and stabilising structure 3400 may comprise at least one strap having a rectangular cross-section. In one example the positioning and stabilising structure 3400 may comprise at least one flat strap.

In one form of the present technology, a positioning and stabilising structure 3400 may be provided that is configured so as not to be too large and bulky to prevent the patient from lying in a supine sleeping position with a back region of the patient's head on a pillow.

In one form of the present technology, a positioning and stabilising structure 3400 may be provided that is configured so as not to be too large and bulky to prevent the patient from lying in a side sleeping position with a side region of the patient's head on a pillow.

In one form of the present technology, a positioning and stabilising structure 3400 may be provided with a decoupling portion located between an anterior portion of the positioning and stabilising structure 3400, and a posterior portion of the positioning and stabilising structure 3400. The decoupling portion may not resist compression and may be, e.g. a flexible or floppy strap. The decoupling portion may be constructed and arranged so that when the patient lies with their head on a pillow, the presence of the decoupling portion may prevent a force on the posterior portion from being transmitted along the positioning and stabilising structure 3400 and disrupting the seal.

In one form of the present technology, a positioning and stabilising structure 3400 may comprise a strap constructed from a laminate of a fabric patient-contacting layer, a foam inner layer and a fabric outer layer. In one form, the foam may be porous to allow moisture, (e.g., sweat), to pass through the strap. In one form, the fabric outer layer may comprise loop material to engage with a hook material portion.

In certain forms of the present technology, a positioning and stabilising structure 3400 may comprise a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure may comprise, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure may include a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure may include a third tie that is constructed and arranged to interconnect the first tie and the second tie to reduce a tendency of the first tie and the second tie to move apart from one another.

In certain forms of the present technology, a positioning and stabilising structure 3400 may comprise a strap that is bendable and e.g. non-rigid. An advantage of this aspect is that the strap may be more comfortable for a patient to lie upon while the patient is sleeping.

In certain forms of the present technology, a positioning and stabilising structure 3400 may comprise a strap constructed to be breathable to allow moisture vapour to be transmitted through the strap, In certain forms of the present technology, a system is provided comprising more than one positioning and stabilizing structure 3400, each being configured to provide a retaining force to correspond to a different size and/or shape range. For example the system may comprise one form of positioning and stabilizing structure 3400 suitable for a large sized head, but not a small sized head, and another. suitable for a small sized head, but not a large sized head.

In the illustrated example, the seal-forming structure 3100 of the patient interface 3000 of the present technology may be held in sealing position in use by the stabilizing structure (headgear) 3400. The headgear 3400 may include a pair of upper side straps 3410 and a pair of lower side straps 3420 connected to a circular crown strap 3430 that encapsulates the crown of the patient's head. The upper side straps 3410 may connect to the upper headgear connector arms 3330 of the frame assembly 3300 and the lower side straps 3420 may connect to the lower headgear connector arms 3335 of the frame assembly 3300, e.g., via headgear clips. The side straps 3410, 3420 may include an adjustable hook and loop (Velcro™) connection mechanism, e.g., Velcro™-like hook tabs, to facilitate connection and/or adjustment. Alternatively, the lower side straps 3420 may include magnetic connectors to engage corresponding magnetic connectors on the lower headgear connector arms 3335 of the frame assembly 3300.

4.3.5 Vent

In one form, the patient interface 3000 may include a vent 3500 constructed and arranged to allow for the washout of exhaled gases, e.g. carbon dioxide.

In certain forms the vent 3500 may be configured to allow a continuous vent flow from an interior of the plenum chamber to ambient whilst the pressure within the plenum chamber is positive with respect to ambient. The vent 3500 may be configured such that the vent flow rate has a magnitude sufficient to reduce rebreathing of exhaled $CO_2$ by the patient while maintaining the therapeutic pressure in the plenum chamber in use.

One form of vent 3500 in accordance with the present technology may comprise a plurality of holes, for example, about 20 to about 80 holes, or about 40 to about 60 holes, or about 45 to about 55 holes.

The vent 3500 may be located in the shell or chassis 3200. Alternatively, the vent 3500 may be located in a decoupling structure, e.g., a swivel.

4.4 Rpt Device

An RPT device 4000 in accordance with one aspect of the present technology comprises mechanical, pneumatic, and/ or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

4.4.1 RPT Device Mechanical & Pneumatic Components

An RPT device may comprise one or more of the following components in an integral unit. In an alternative form, one or more of the following components may be located as respective separate units.

4.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000 or 3800.

4.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000 or 3800.

4.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$ when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

4.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000 or 3800.

In one form, a signal from a transducer 4270 may be filtered, such as by low-pass, high-pass or band-pass filtering.

4.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal generated by the flow rate sensor 4274 and representing a flow rate is received by the central controller 4230.

4.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal generated by the pressure sensor 4272 is received by the central controller 4230.

4.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

4.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

4.4.2 RPT Device Electrical Components 4.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

4.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

4.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

4.4.2.4 Clock

The RPT device 4000 may include a clock 4232 that is connected to the central controller 4230.

4.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

4.4.2.6 Protection Circuits

The one or more protection circuits 4250 in accordance with the present technology may comprise an electrical protection circuit, a temperature and/or pressure safety circuit.

4.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

4.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

4.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

4.4.2.9.1 Display Driver

A display driver 4292 receives as an input the characters, symbols, or images intended for display on the display 4294, and converts them to commands that cause the display 4294 to display those characters, symbols, or images.

4.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

4.5 Air Circuit

An air circuit 4170 in accordance with an aspect of the present technology is a conduit or a tube constructed and arranged to allow, in use, a flow of air to travel between two components such as RPT device 4000 and the patient interface 3000 or In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

4.5.1 Supplementary Gas Delivery

In one form of the present technology, supplementary gas, e.g. oxygen, 4180 is delivered to one or more points in the pneumatic path, such as upstream of the pneumatic block 4020, to the air circuit 4170, and/or to the patient interface 3000 or 3800.

4.6 Humidifier 4.6.1 Humidifier Overview

In one form of the present technology there is provided a humidifier 5000 (e.g. as shown in FIG. 54) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 54 and FIG. 55, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

4.6.2 Humidifier Components 4.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 54 and FIG. 55.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

4.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

4.6.2.3 Humidifier Reservoir Dock

In one form, the humidifier 5000 may comprise a humidifier reservoir dock 5130 (as shown in FIG. 55) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

4.6.2.4 Water Level Indicator

The humidifier reservoir 5110 may comprise a water level indicator 5150 as shown in FIG. 54-55. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

4.6.2.5 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 56. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

4.6.2.5.1 Pressure Transducer

One or more pressure transducers 5212 may be provided to the humidifier 5000 in addition to, or instead of, a pressure sensor 4272 provided in the RPT device 4000.

4.6.2.5.2 Flow Rate Transducer

One or more flow rate transducers 5214 may be provided to the humidifier 5000 in addition to, or instead of, a flow rate sensor 4274 provided in the RPT device 4000.

4.6.2.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

4.6.2.5.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

4.6.2.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 55.

4.6.2.7 Humidifier Controller

According to one arrangement of the present technology, a humidifier 5000 may comprise a humidifier controller 5250 as shown in FIG. 56. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 56, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

4.7 Glossary

For the purposes of the present technology disclosure, in certain forms of the present technology, one or more of the following definitions may apply. In other forms of the present technology, alternative definitions may apply.

4.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/cm$^2$ and hectopascal. 1 $cmH_2O$ is equal to 1 g-f/cm$^2$ and is approximately 0.98 hectopascal (1 hectopascal=100 Pa=100 N/m$^2$=1 millibar 0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

4.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240-15e1.

Polycarbonate: a thermoplastic polymer of Bisphenol-A Carbonate.

4.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

4.7.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of Flow Limited Inspiratory Waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

4.7.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired interface pressure which the ventilator will attempt to achieve at a given time.

End expiratory pressure (EEP): Desired interface pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired interface pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

4.7.4 Anatomy 4.7.4.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 4.7.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

4.7.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

4.7.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Functional dead space: portion of plenum chamber in which $CO_2$ is able to collect without being washed out.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

4.7.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 27 to FIG. 31, which illustrate examples of cross-sections at point p on a surface, and the resulting plane curves. FIGS. 27 to 31 also illustrate an outward normal vector at p. The outward normal vector at p points away from the surface. In some examples we describe the surface from the point of view of an imaginary small person standing upright on the surface.

4.7.6.1 Curvature in One Dimension

The curvature of a plane curve at p may be described as having a sign (e.g. positive, negative) and a magnitude (e.g. 1/radius of a circle that just touches the curve at p).

Figure 1:
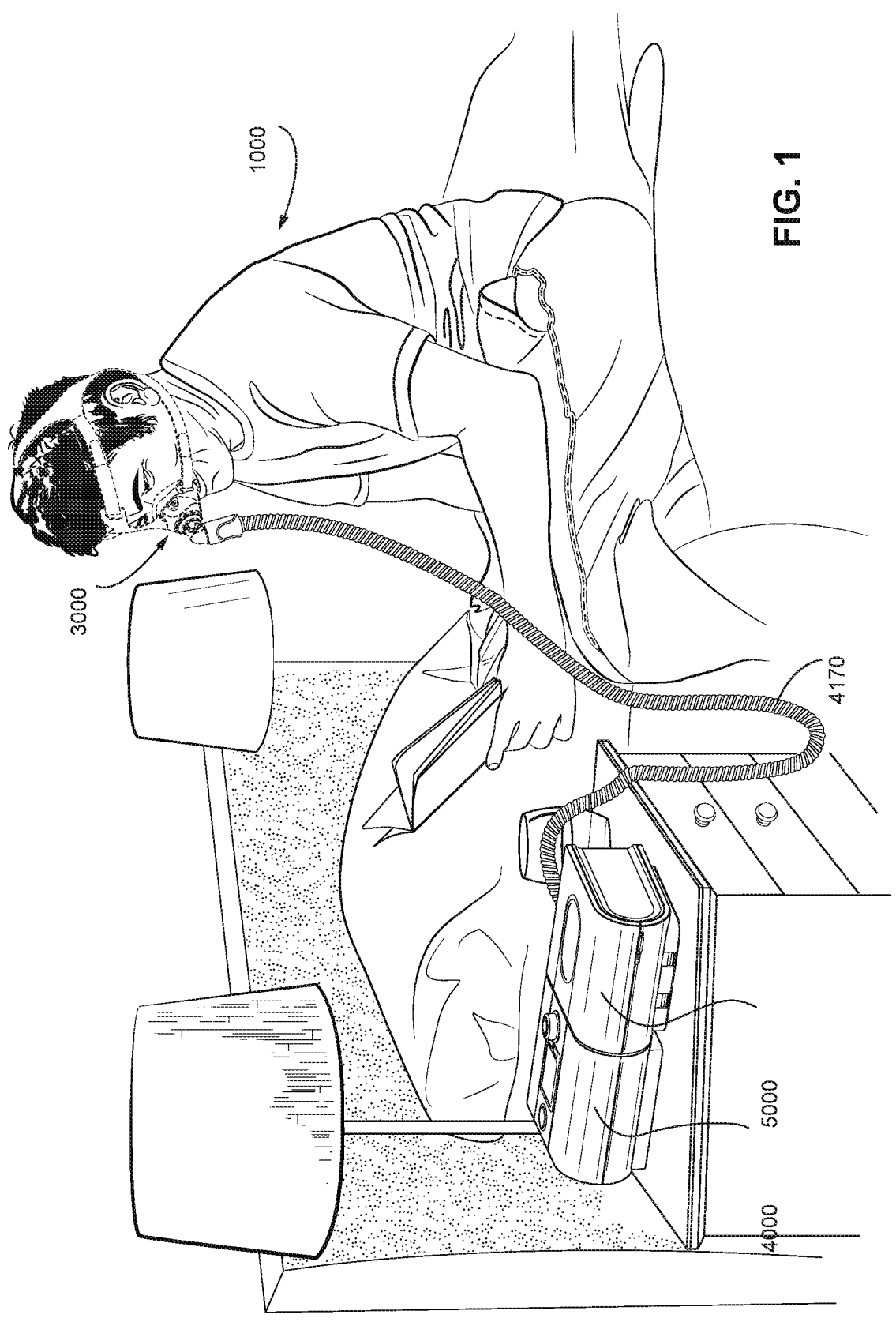
Figure 2:
Figure 3:
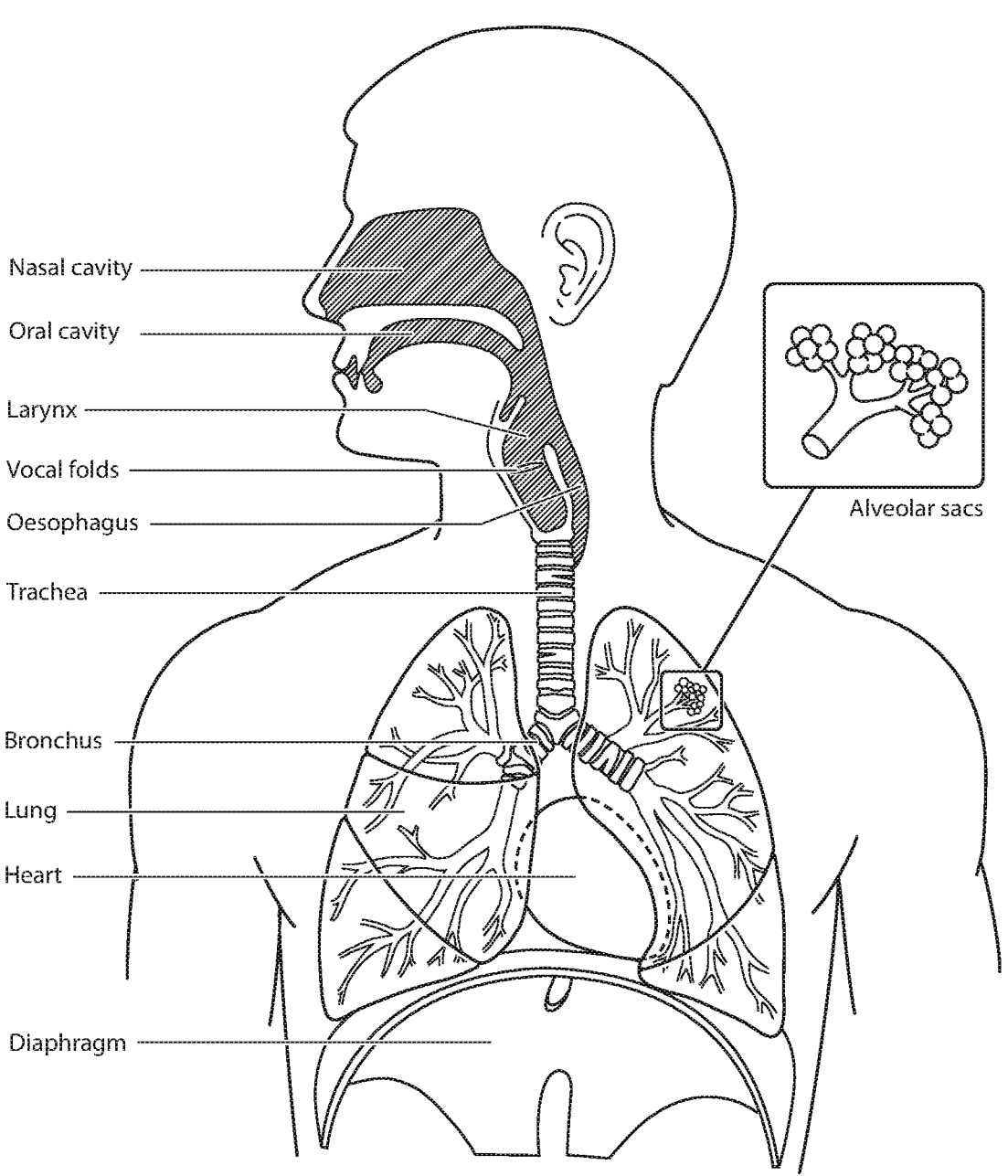
FIG. 3 shows an overview of a human respiratory system including the nasal and oral cavities, the larynx, vocal folds, oesophagus, trachea, bronchus, lung, alveolar sacs, heart and diaphragm.
Figure 4:
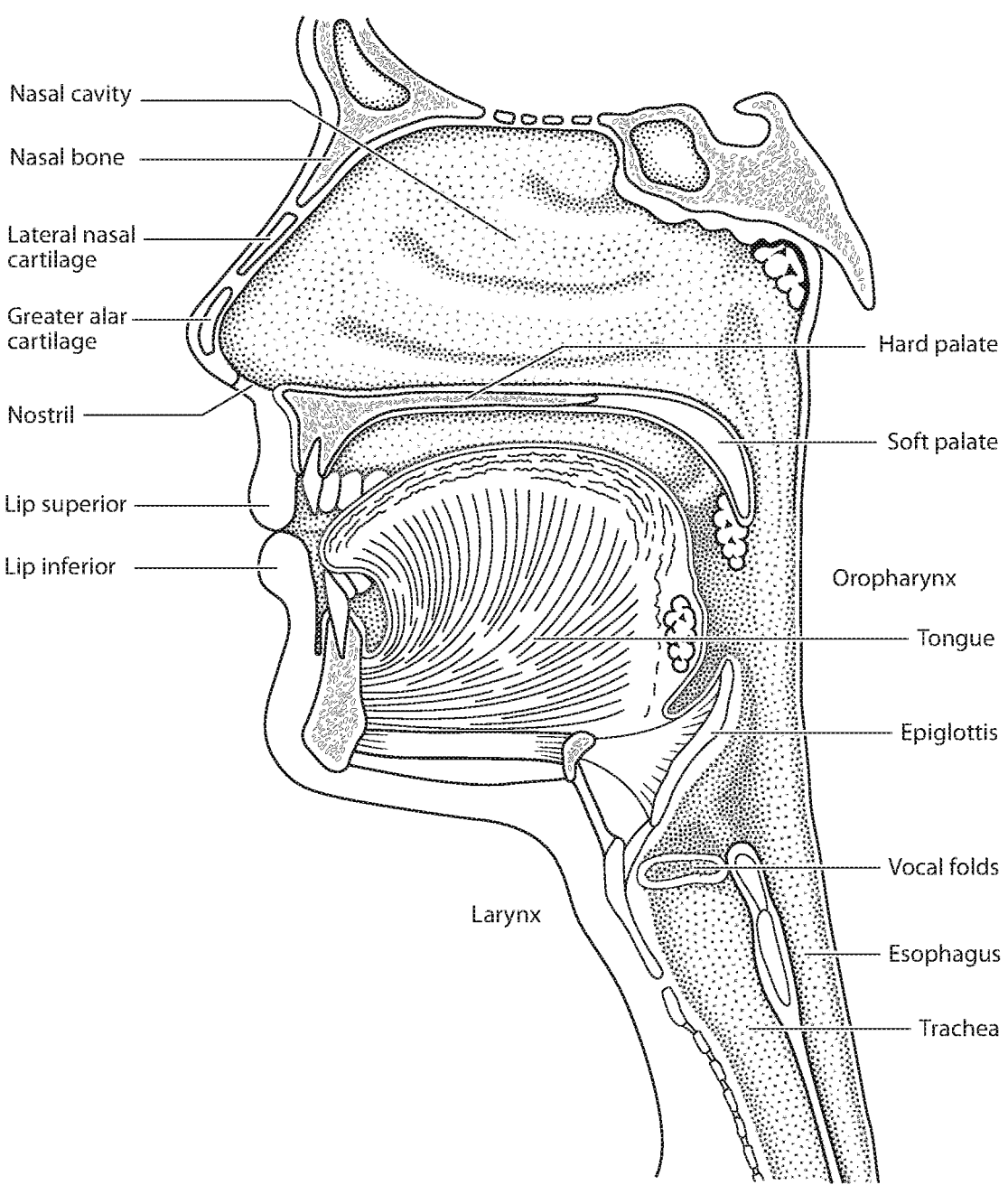
FIG. 4 shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 5:
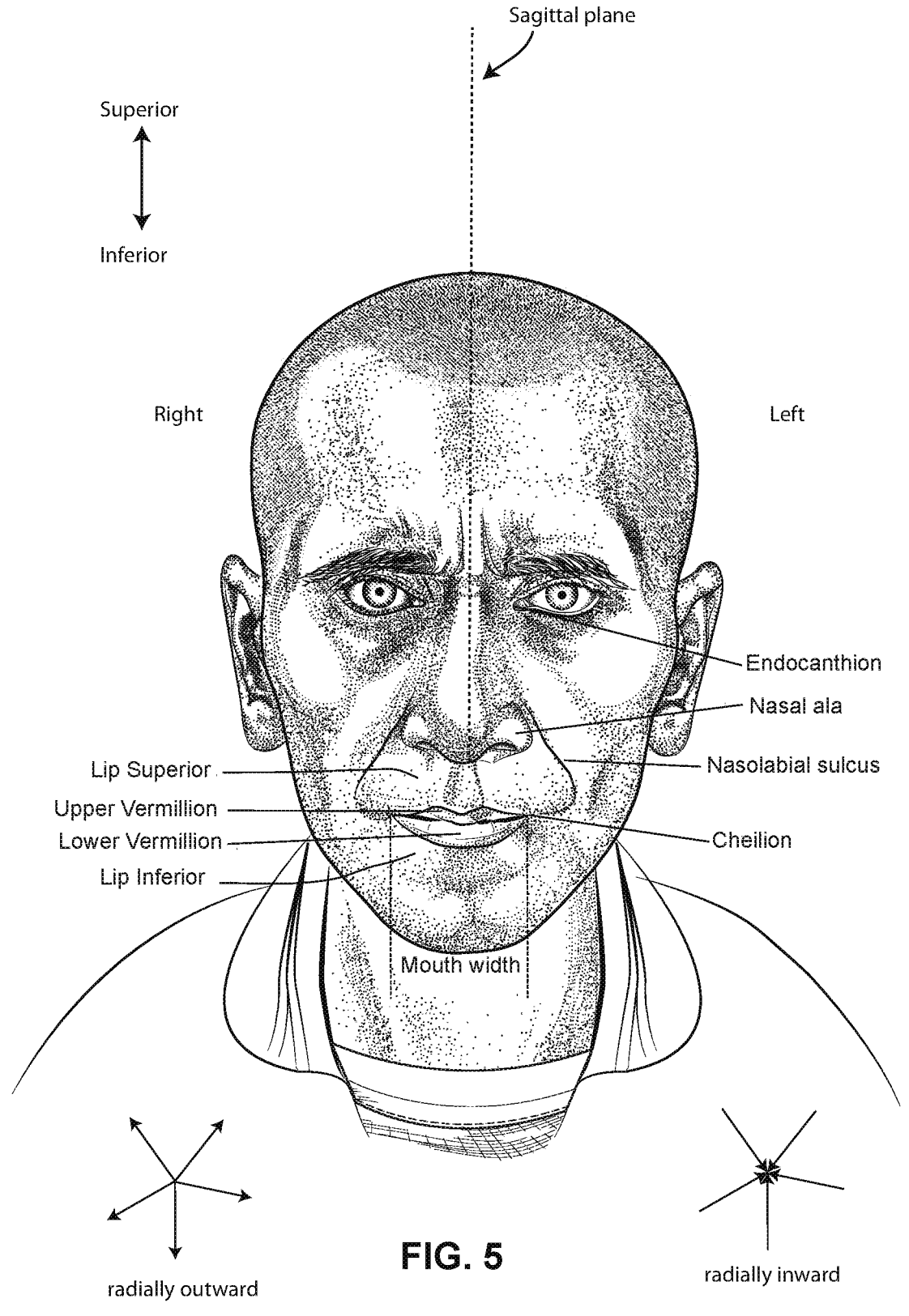
FIG. 5 is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 6:
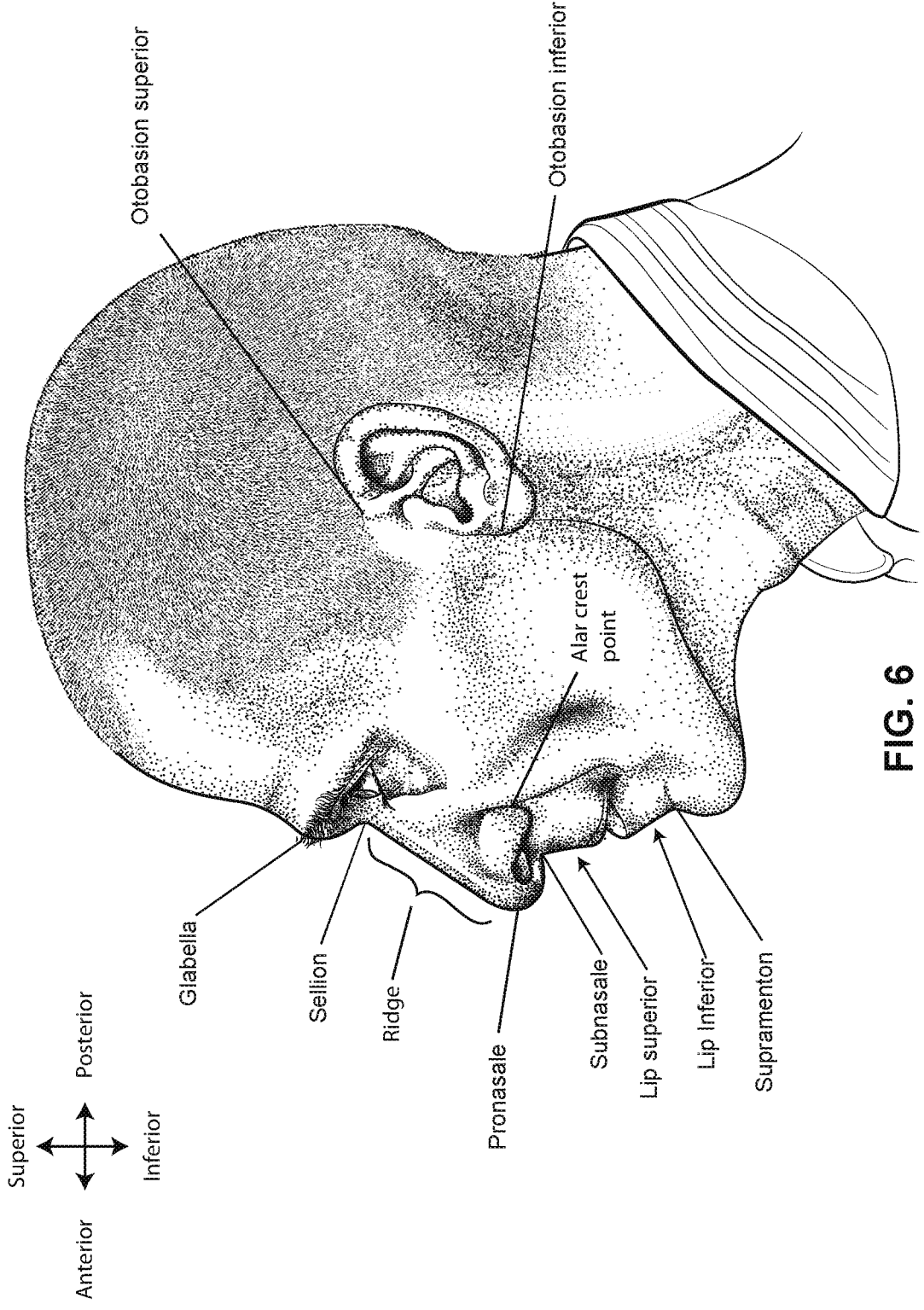
FIG. 6 is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Positive curvature: If the curve at p turns towards the outward normal, the curvature at that point will be taken to be positive (if the imaginary small person leaves the point p they must walk uphill). See FIG. 27 (relatively large positive curvature compared to FIG. 28) and FIG. 28 (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 29.

Negative curvature: If the curve at p turns away from the outward normal, the curvature in that direction at that point will be taken to be negative (if the imaginary small person leaves the point p they must walk downhill). See FIG. 30 (relatively small negative curvature compared to FIG. 31) and FIG. 31 (relatively large negative curvature compared to FIG. 30). Such curves are often referred to as convex.

4.7.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 27 to 31 could be examples of such multiple cross-sections at a particular point.

Principal curvatures and directions: The directions of the normal planes where the curvature of the curve takes its maximum and minimum values are called the principal directions. In the examples of FIG. 27 to FIG. 31, the maximum curvature occurs in FIG. 27, and the minimum occurs in FIG. 31, hence FIG. 27 and FIG. 31 are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

4.7.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 42. A typical human right ear comprises a helix, which is a right-hand helix, see FIG. 43. FIG. 44 shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 41), or alternatively by a left-hand rule (FIG. 40).

Osculating plane: The plane containing the unit tangent vector and the unit principal normal vector. See FIGS. 40 and 41.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 44, since T2>T1, the magnitude of the torsion near the top coils of the helix of FIG. 44 is greater than the magnitude of the torsion of the bottom coils of the helix of FIG. 44.

With reference to the right-hand rule of FIG. 41, a space curve turning towards the direction of the right-hand binormal may be considered as having a right-hand positive torsion (e.g. a right-hand helix as shown in FIG. 44). A space curve turning away from the direction of the right-hand binormal may be considered as having a right-hand negative torsion (e.g. a left-hand helix).

Equivalently, and with reference to a left-hand rule (see FIG. 41), a space curve turning towards the direction of the left-hand binormal may be considered as having a left-hand positive torsion (e.g. a left-hand helix). Hence left-hand positive is equivalent to right-hand negative. See FIG. 45.

4.7.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 34, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 37 and the example cross-sections there-through in FIG. 38 and FIG. 39, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 36, bounded by a surface as shown.

4.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

4.9 REFERENCE SIGNS LIST

| patient | 1000 |
| bed partner | 1100 |
| patient interface | 3000 |
| seal-forming structure | 3100 |
| foam cushion | 3105 |
| undercushion | 3110 |
| sealing surface | 3115 |
| attachment surface | 3120 |
| hole | 3125 |
| inner surface | 3126 |
| perimeter surface | 3127 |
| first rim | 3130 |
| second rim | 3135 |
| central superior region | 3140 |
| central inferior region | 3142 |
| widened regions | 3145 |
| widened regions | 3150 |
| bisecting plane | 3155 |
| lower corner regions | 3156 |
| top side regions | 3157 |
| intermediate regions | 3158 |
| support wall | 3160 |
| lateral axis | 3161 |
| outer surface | 3162 |
| support flange | 3165 |
| superior gusset | 3170 |
| thickened regions | 3175 |
| inferior gusset | 3180 |
| lateral axis | 3185 |
| ribs | 3190 |
| extended region | 3195 |
| lower corner regions | 3196 |
| top side regions | 3197 |
| intermediate region | 3198 |
| intermediate region | 3199 |
| chassis | 3200 |
| plenum chamber | 3205 |
| chord | 3210 |
| opening | 3211 |
| axis | 3212 |
| frankfort horizontal plane | 3213 |
| annular flange | 3215 |
| superior point | 3220 |
| lip seal | 3225 |
| inferior point | 3230 |
| frame assembly | 3300 |
| shroud | 3305 |
| headgear connector | 3310 |
| opening | 3315 |
| spring arms | 3320 |
| shroud connection portion | 3325 |
| upper headgear connector arms | 3330 |
| lower headgear connector arms | 3335 |
| intermediate portions | 3340 |
| upper headgear attachment points | 3345 |
| magnetic connector | 3350 |
| flexible portion | 3355 |
| stabilising structure | 3400 |
| upper side straps | 3410 |
| lower side straps | 3420 |
| circular crown strap | 3430 |
| vent | 3500 |
| ISO | 3744 |
| RPT device | 4000 |
| external housing | 4010 |
| upper portion | 4012 |
| portion | 4014 |
| panel | 4015 |
| chassis | 4016 |
| handle | 4018 |
| pneumatic block | 4020 |

-continued

| air filters | 4110 |
| inlet air filter | 4112 |
| outlet air filter | 4114 |
| mufflers | 4120 |
| inlet muffler | 4122 |
| outlet muffler | 4124 |
| pressure generator | 4140 |
| blower | 4142 |
| motor | 4144 |
| anti-spill back valve | 4160 |
| air circuit | 4170 |
| electrical components | 4200 |
| PCBA | 4202 |
| power supply | 4210 |
| input devices | 4220 |
| central controller | 4230 |
| clock | 4232 |
| therapy device controller | 4240 |
| protection circuits | 4250 |
| memory | 4260 |
| transducers | 4270 |
| pressure sensor | 4272 |
| flow rate sensors | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| algorithms | 4300 |
| therapy control module | 4330 |
| humidifier | 5000 |
| humidifier inlet | 5002 |
| humidifier outlet | 5004 |
| humidifier base | 5006 |
| reservoir | 5110 |
| conductive portion | 5120 |
| humidifier reservoir dock | 5130 |
| locking lever | 5135 |
| water level indicator | 5150 |
| humidifier transducers | 5210 |
| pressure transducers | 5212 |
| flow rate transducers | 5214 |
| temperature sensor | 5216 |
| humidity sensor | 5218 |
| heating element | 5240 |
| humidifier controller | 5250 |
| central humidifier controller | 5251 |
| heating element controller | 5252 |
| air circuit controller | 5254 |

The invention claimed is:

1. A patient interface configured to deliver a flow of positive pressure respiratory gas to an entrance of a patient's airways including at least an entrance of the patient's nares, the patient interface being configured to maintain a therapy pressure in a range of about 4 cmH2O to about 30 cmH2O above ambient pressure in use, throughout the patient's respiratory cycle, while the patient is sleeping, to ameliorate sleep disordered breathing, the patient interface comprising:

an elastomeric support wall forming at least part of a plenum chamber configured to receive the flow of positive pressure respiratory gas, the elastomeric support wall comprising a pair of thickened regions on opposing sides of a plane that bisects the elastomeric support wall and extends from the superior side of the elastomeric support wall to the inferior side of the elastomeric support wall;

an elastomeric support flange positioned at an end of the elastomeric support wall and extending radially inward from the support wall, the support flange comprising a flap portion at a central superior region of the support flange that extends further in the radially inward direction than the rest of the support flange; and a foam cushion being mounted on the support flange, the foam cushion being configured to form a seal with the patient's face and comprising an attachment surface that is in contact with an outer surface of the support flange, wherein the thickness of the elastomeric support wall is greatest in the pair of thickened regions, and wherein the increased thickness of the thickened regions of the elastomeric support wall does not extend into the elastomeric support flange.

2. The patient interface of claim 1, wherein the attachment surface of the foam cushion is widest at a location corresponding to the flap portion.

3. The patient interface of according to claim 1, wherein the outer surface of the support flange at the flap portion has a positive curvature.

4. The patient interface of claim 3, wherein a central inferior region of the support flange has a positive curvature.

5. The patient interface of claim 4, wherein the curvature of the support flange in the flap portion is larger than the curvature of the support flange in the central inferior region.

6. The patient interface of claim 1, wherein the central inferior region of the support flange is between a first pair of negative curvature regions of the support flange.

7. The patient interface of claim 1, wherein the flap portion is between a second pair of negative curvature regions of the support flange.

8. The patient interface of claim 1, wherein the support flange comprises eight transition regions in which the curvature of the outer surface of the support flange transitions from positive to negative or negative to positive.

9. The patient interface of claim 1, wherein the foam cushion comprises a sealing surface configured to be in contact with the patient's face in use, wherein the sealing surface of the foam cushion has a positive curvature at locations where the outer surface of the support flange has a positive curvature, and wherein the sealing surface of the foam cushion has a negative curvature at locations where the outer surface of the support flange has a negative curvature.

10. The patient interface of claim 1, wherein the outer surface of the support flange in the flap portion has a saddle shape.

11. The patient interface of claim 1, wherein the outer surface of the support flange in the central inferior region has a saddle shape.

12. The patient interface of claim 1, wherein the outer surface of the support flange in the flap portion is between a first pair of dome regions.

13. The patient interface of claim 1, wherein the outer surface of the support flange in the central inferior region is between a second pair of dome regions.

14. The patient interface of claim 1, wherein the foam cushion overhangs the support flange.

15. The patient interface of claim 1, further comprising a shell with an inlet opening configured to receive the flow of positive pressure respiratory gas, the support wall being mounted to the shell.

16. The patient interface of claim 15, further comprising a positioning and stabilizing structure configured to support the shell, the support wall, and the foam cushion on the patient's head, the positioning and stabilizing structure being removably attachable to the shell.

17. The patient interface of claim 16, wherein the positioning and stabilizing structure comprises a shroud and a plurality of headgear straps.

18. The patient interface of claim 17, wherein the shroud is removably attachable to the shell at the inlet opening.

19. The patient interface of claim 18, further comprising an air delivery tube connectable to the shroud and the shell.

20. A patient interface configured to deliver a flow of positive pressure respiratory gas to an entrance of a patient's airways including at least an entrance of the patient's nares, the patient interface being configured to maintain a therapy pressure in a range of about 4 cmH2O to about 30 cmH2O above ambient pressure in use, throughout the patient's respiratory cycle, while the patient is sleeping, to ameliorate sleep disordered breathing, the patient interface comprising:

an elastomeric support wall forming at least part of a plenum chamber configured to receive the flow of positive pressure respiratory gas;

an elastomeric support flange positioned at an end of the elastomeric support wall and extending radially inward from the support wall; and a foam cushion mounted on the support flange, the foam cushion being configured to form a seal with the patient's face, wherein an elastomeric wall thickness of the support flange varies from a central superior region of the support flange to a central inferior region of the support flange, wherein the thickness of the elastomeric support wall is greatest in a thickened region, and wherein the increased thickness of the thickened region of the elastomeric support wall does not extend into the elastomeric support flange.

21. The patient interface of claim 20, wherein the elastomeric wall thickness of the support flange is thinner at the central superior region and the central inferior region than in intermediate regions between the central superior region and the central inferior region.

22. The patient interface of claim 20, wherein the elastomeric wall thickness of the support flange is thinner at the central superior region than at the central inferior region.

23. The patient interface of claim 20, wherein an elastomeric wall thickness of the support wall varies from a central superior region of the support wall to a central inferior region of the support wall.

24. The patient interface of claim 23, wherein the elastomeric wall thickness of the support wall is thinner at the central superior region of the support wall and at the central inferior region of the support wall than at intermediate regions between the central superior region and the central inferior region.

25. The patient interface of claim 23, wherein the elastomeric wall thickness of the support wall is thinner at the central superior region than at the central inferior region.

26. The patient interface of claim 20, wherein the central superior region of the support wall comprises a superior gusset, and the central inferior region of the support wall comprises an inferior gusset.

27. The patient interface of claim 26, wherein the inferior gusset is more collapsible than the superior gusset.

28. The patient interface of claim 20, wherein a thickness of the foam cushion is consistent throughout the foam cushion.

29. The patient interface of claim 20, further comprising a pair of compressible ribs at an inferior region of the patient interface, each of the compressible ribs being attached to the support wall and the support flange and being configured to prevent at least a portion of the support flange from flexing due to positive pressure in the plenum chamber.

30. The patient interface of claim 20, wherein the support flange comprises a flap portion at the central superior region of the support flange that extends further in the radially inward direction than the rest of the support flange, and wherein the flap portion is configured to prevent at least a portion of the support flange from flexing due to positive pressure in the plenum chamber.

31. The patient interface of claim 20, wherein the foam cushion overhangs the support flange.

32. The patient interface of claim 20, wherein the foam cushion comprises an attachment surface configured to be attached to the support flange and comprises a sealing surface configured to contact and form a seal with the patient's face, wherein the foam cushion is bent around a bisecting plane that bisects the foam cushion and extends through the central superior region and the central inferior region of the foam cushion, and wherein the attachment surface and the sealing surface are wider at the bisecting plane than at the remaining portions of the foam cushion.

33. The patient interface of claim 32, wherein the foam cushion comprises a perimeter surface extending from the attachment surface to the sealing surface, and wherein the perimeter surface is concave at the central inferior region.

34. The patient interface of claim 20, further comprising a shell with an inlet opening configured to receive the flow of positive pressure respiratory gas, the support wall being mounted to the shell.

35. The patient interface of claim 34, further comprising a positioning and stabilizing structure configured to support the shell, the support wall, and the foam cushion on the patient's head, the positioning and stabilizing structure being removably attachable to the shell.

36. The patient interface of claim 35, wherein the positioning and stabilizing structure comprises a shroud and a plurality of headgear straps.

37. The patient interface of claim 36, wherein the shroud is removably attachable to the shell at the inlet opening.

38. The patient interface of claim 37, further comprising an air delivery tube connectable to the shroud and the shell.

39. A patient interface configured to deliver a flow of positive pressure respiratory gas to an entrance of a patient's airways including at least an entrance of the patient's nares, the patient interface being configured to maintain a therapy pressure in a range of about 4 cmH2O to about 30 cmH2O above ambient pressure in use, throughout the patient's respiratory cycle, while the patient is sleeping, to ameliorate sleep disordered breathing, the patient interface comprising:
    a shell with an inlet opening configured to receive the flow of positive pressure respiratory gas;
    an elastomeric support wall mounted to the shell, the shell and the elastomeric support wall together forming at least part of a plenum chamber configured to receive the flow of positive pressure respiratory gas, the elastomeric support wall comprising a pair of thickened regions on opposing sides of a plane that bisects the elastomeric support wall and extends from the superior side of the elastomeric support wall to the inferior side of the elastomeric support wall;
an elastomeric support flange positioned at an end of the elastomeric support wall and extending radially inward from the support wall; and
a foam cushion mounted on the support flange, the foam cushion being configured to form a seal with the patient's face,
wherein the inlet opening has a central longitudinal axis that extends through an anterior aperture configured to receive the patient's nose, and
wherein the elastomeric support wall and the foam cushion are configured so that when the patient interface is mounted on the patient's face, a part of the central longitudinal axis extending outwardly from the anterior side of the patient interface extends in an inferior direction,
wherein the thickness of the elastomeric support wall is greatest in the pair of thickened regions, and
wherein the increased thickness of the thickened regions of the elastomeric support wall does not extend into the elastomeric support flange.

40. The patient interface of claim 39, wherein the support wall is configured to pivot around a lateral axis that extends through lateral sides of the support wall.

41. The patient interface of claim 40, wherein an inferior portion of the support wall comprises an inferior gusset, and the inferior gusset is configured so that the support wall flexes around the lateral axis when the inferior gusset is collapsed.

42. The patient interface of claim 39, wherein a superior portion of the support wall comprises a superior gusset.

43. The patient interface of claim 39, further comprising a positioning and stabilizing structure configured to support the shell, the support wall, and the foam cushion on the patient's head, the positioning and stabilizing structure being removably attachable to the shell.

44. The patient interface of claim 43, wherein the positioning and stabilizing structure comprises a shroud and a plurality of headgear straps.

45. The patient interface of claim 44, wherein the shroud is removably attachable to the shell at the inlet opening.

46. The patient interface of claim 45, further comprising an air delivery tube connectable to the shroud and the shell.

* * * * *